United States Patent
Mattsby-Baltzer et al.

(10) Patent No.: US 8,318,448 B2
(45) Date of Patent: Nov. 27, 2012

(54) **DIAGNOSIS OF CANDIDIASIS AND CANDIDEMIA OR INVASIVE *CANDIDA* INFECTION**

(75) Inventors: Inger Mattsby-Baltzer, Förtroligheten (SE); Nahid Kondori, Smedsbacken (SE)

(73) Assignee: Fungea AB, Gothenburg (SE)

( * ) Notice: Subject to any disclaimer, the term of this patent is extended or adjusted under 35 U.S.C. 154(b) by 431 days.

(21) Appl. No.: 12/454,509

(22) Filed: May 19, 2009

(65) Prior Publication Data

US 2009/0305313 A1    Dec. 10, 2009

Related U.S. Application Data

(62) Division of application No. 10/532,042, filed as application No. PCT/SE03/01639 on Oct. 21, 2003, now abandoned.

(51) Int. Cl.
G01N 33/53    (2006.01)
G01N 33/00    (2006.01)

(52) U.S. Cl. ......... 435/7.31; 435/7.92; 435/7.2; 435/7.1

(58) Field of Classification Search .................. None
See application file for complete search history.

(56) References Cited

U.S. PATENT DOCUMENTS

2001/0051717 A1    12/2001    Wakshull et al.

OTHER PUBLICATIONS

Kondori et al. Clin. Diagn. Lab. Immunol. 13: 344-350, Mar. 2004.*
Kondori et al. Medical Mycology 41: 21-30, 2003.*
Nielsen et al. Clinical Microbiology and Infection 16: 855-862, 2010.*
Wong et al. Hybridoma 27: 361-373, 2008.*
Paulovicova et al. Mykosen 29: 393-398, 1986, abstract.*
Karwowska et al. Immunology Letters 8: 127-129, 1984, abstract.*
Karwowska et al. Annales d'Immunologie (Paris) 135D: 145-159, 1984, abstract.*
Rimek et al. Mycoses 47: 27-31, 2004, abstract.*
De Repentigny, L. et al., Comparison of serum mannan, arabinitol, and mannose in experimental disseminated candidiasis, J. Clin. Microbiol. 1984, 19(6):804-812.
Hammarstrom, L. et al., IgG subclass distribution of antibodies against *S. aureus* teichoic acid and alpha-toxin in normal and immuno . . . , Clin. exp. Immunol., 1984, 55:593-601.
Han, Y. et al., Protection against candidiasis by an immunoglobulin G3 (IgG3) monoclonal antibody specific for the same . . . , Infection & Immunity, 2000, 68:1649-1654.
Hayette, MP et al., Presence of human antibodies reacting with *Candida albicans* O-linked oligomannosides revealed by using an . . . , J. Clin. Microbiol. 1992, 30:411-417.
Jones, J et al., Laboratory diagnosis of invasive candidiasis, Clin. Microbiol. Reviews, 1990, 3(1):32-45.
Kanbe, T. et al., Evidence for the presence of immunoglobulin E antibodies specific to the cell wall phosphomannoproteins . . . , Clin. & Diag. Lab. Immunol. 1996, 3(6):645-650.
Nakamura, A et al., Diagnosis of invasive candidiasis by detection of mannan antigen by using the avidin-botin enzyme immunoassay, J. Clin. Microbiol. 1991, 29(11):2363-67.
Sendid, B. et al., New enzyme immunoassays for sensitive detection of circulating *Candida albicans* mannan and antimannan . . . , J. Clin. Microbiol. 1999, 37(5):1510-17.
Zoller, L et al., Enzyme immunoassays for invasive *Candida* infections: Reactivity of somatic antigens of *Candida albicans*, J. Clin. Microbiol. 1991, 25(9):1860-67.

* cited by examiner

*Primary Examiner* — S. Devi
(74) *Attorney, Agent, or Firm* — Lynn E. Barber

(57) ABSTRACT

The use of an antibody to a *C. albicans* cell wall antigen or to a solubilized phosphopeptidomannan (PPM) fraction of the cell wall of *C. albicans*, or preferably a combination of an IgG2 antibody to a phosphopeptidomannan (PPM) fraction of the cell wall of *C. albicans*, and an IgG1 or IgG3 antibody to a *C. albicans* cell wall antigen in the diagnosis of candidiasis or invasive candidiasis is disclosed. Also diagnostic tests are disclosed.

1 Claim, 19 Drawing Sheets

SIGNIFICANCE VS.
  I:     *      **     *
  II:         *    **

SIGNIFICANCE VS.
I:  NS    **    *
II: NS    NS    NS

DIAGNOSIS OF CANDIDIASIS AND CANDIDEMIA OR INVASIVE *CANDIDA* INFECTION

CROSS-REFERENCE TO RELATED APPLICATIONS

This application is a divisional application of U.S. application serial number 10/532,042 filed Feb. 6, 2006 (now abandoned), which is a 371 of PCT/SE2003/01639, filed Oct. 21, 2003, which claims priority from SE 0203099-7, filed Oct. 21, 2002.

FIELD OF THE INVENTION

The present invention relates to the use of *Candida albicans* cell wall antigens for serological diagnosis of systemic candidiasis, including IgG subclass antibodies to *C. albicans* cell wall antigens.

BACKGROUND OF THE INVENTION

Invasive candidosis is difficult to diagnose and is the cause of substantial morbidity and mortality in immunosuppressed patients. The clinical symptoms are often vague and conventional blood culturing is often negative [de Repentigny L, Kuykendall R. J, Chandler F. W, Broderson J. R, Reiss E. Comparison of serum mannan, arabinitol, and mannose in experimental disseminated candidiasis. J Clin Microbiol, 1984. 19(6): p. 804-12; Gutierrez J, Maroto C, Piedrola G, Martin E, Perez J. A. Circulating *Candida* antigens and antibodies: useful markers of candidemia. J Clin Microbiol, 1993. 31(9): p. 2550-2; Jones, J. M., Laboratory diagnosis of invasive candidiasis. Clin Microbiol Rev, 1990. 3(1): p. 32-45]. Laboratory diagnosis of deep *Candida* infection is based on blood culturing, direct microscopy, and determination of *Candida* antigens. Anti-*Candida* antibodies and detection of D-arabinitol in serum or urine by gas liquid chromatography are complementary analyses [de Repentigny L, Kuykendall R. J, Chandler F. W, Broderson J. R, Reiss E. Comparison of serum mannan, arabinitol, and mannose in experimental disseminated candidiasis. J Clin Microbiol, 1984. 19(6): p. 804-12; Gutierrez J, Maroto C, Piedrola G, Martin E, Perez J. A. Circulating *Candida* antigens and antibodies: useful markers of candidemia. J Clin Microbiol, 1993. 31(9): p. 2550-2; Fujita, S, Hashimoto T, Detection of serum *Candida* antigens by enzyme-linked immunosorbent assay and a latex agglutination test with anti-*Candida albicans* and anti-*Candida krusei* antibodies. J Clin Microbiol, 1992. 30(12): p. 3132-7; Nakamura A, Ishikawa N, Suzuki H. Diagnosis of invasive candidiasis by detection of mannan antigen by using the avidin-biotin enzyme immunoassay. J Clin Microbiol, 1991. 29(11): p. 2363-7].

Antibody determination for immunodiagnosis of systemic candidosis includes latex agglutination [Dee T. H., Johnson G. M, Berger C. S. Sensitivity, specificity, and predictive value of anti-candida serum precipitin and agglutinin quantification: comparison of counterimmunoelectrophoresis and latex agglutination. J Clin Microbiol, 1981. 13(4): p. 750-3], counterimmunoelectrophoresis [Bisbe J, Miro J. M, Torres J. M, Latorre X, Alia C, Amaral M, Estivill D, Mallolas J, Trilla A, Soriano E. Diagnostic value of serum antibody and antigen detection in heroin addicts with systemic candidiasis. Rev Infect Dis, 1989. 11(2): p. 310-5; Kostiala, A. A. and I. Kostiala. Enzyme-linked immunosorbent assay (ELISA) for IgM, IgG and IgA class antibodies against *Candida albicans* antigens: development and comparison with other methods. Sabouraudia, 1981. 19(2): p. 123-34], indirect immunofluorescence [Quindos G, Ponton J, Cisterna R. Detection of antibodies to *Candida albicans* germ tube in the diagnosis of systemic candidiasis. Eur J Clin Microbiol, 1987. 6(2): p. 142-6] and enzyme-linked immunoassay [Kostiala, A. A. and I. Kostiala. Enzyme-linked immunosorbent assay (ELISA) for IgM, IgG and IgA class antibodies against *Candida albicans* antigens: development and comparison with other methods. Sabouraudia, 1981. 19(2): p. 123-34; Greenfield R. A., Bussey, M. J, Stephens J. L, Jones J. M. Serial enzyme-linked immunosorbent assays for antibody to *Candida* antigens during induction chemotherapy for acute leukemia. J Infect Dis, 1983. 148(2): p. 275-83; Navarro D, Monzonis E., Lopez-Ribot J. L, Sepulveda P, Casanova M, Nogueira J. M, Martinez J. P. Diagnosis of systemic candidiasis by enzyme immunoassay detection of specific antibodies to mycelial phase cell wall and cytoplasmic candidal antigens. Eur J Clin Microbiol Infect Dis, 1993. 12(11): p. 839-46]. The antibody tests often express a low sensitivity, i.e. in most cases they fail to discriminate between disseminated and superficial candidosis [Martinez J. P, Gil M. L, Lopez-Ribot J. L., Chaffin W. L. Serologic response to cell wall mannoproteins and proteins of *Candida albicans*. Clin Microbiol Rev, 1998. 11(1): p. 121-41]. In order to increase the specificity of the immunodiagnostic tests, various forms of antigens from *C. albicans* including cytoplasmic extract and cell wall antigens [Sendid, B, Tabouret M., Poirot J. L, Mathieu D, Fruit J, Poulain D. New enzyme immunoassays for sensitive detection of circulating *Candida albicans* mannan and anti-mannan antibodies: useful combined test for diagnosis of systemic candidiasis. J Clin Microbiol, 1999. 37(5): p. 1510-7; Zoller L, Kramer I, Kappe R, Sonntag H. G. Enzyme immunoassays for invasive *Candida* infections: reactivity of somatic antigens of *Candida albicans*. J Clin Microbiol, 1991. 29(9): p. 1860-7] have been used.

The cell wall of *C. albicans* makes up approximately 30% of the total weight of the cell and is composed of carbohydrate (glucan, mannan, and chitin), small amounts of protein, and lipids. The outermost layer of the cell wall is composed of mannoprotein while the deeper layer is made up of β-glucan and chitin microfibrils [Reiss E., Hearn V. M, Poulain D, Shepherd M. G. *Structure and function of the fungal cell wall. J Med* Vet Mycol, 1992. 30(Suppl 1): p. 143-56]. Mannoprotein is a complex glycoprotein composed of mannose polymers and oligomers attached in various ways to a peptide. Mannose or unbranched mannose oligomers are also attached directly to a peptide via the hydroxyl groups of serine or threonine residues [Nelson R. D, Shibata N, Podzorski R. P, Herron M. J. *Candida* mannan: chemistry, suppression of cell-mediated immunity, and possible mechanisms of action. Clin Microbiol Rev, 1991. 4(1): p. 1-19].

Anti-mannan antibodies appear to be one of the major anti-*Candida* antibodies in human sera [Jones J. M. Quantitation of antibody against cell wall mannan and a major cytoplasmic antigen of *Candida* in rabbits, mice, and humans. Infect Immun, 1980. 30(1): p. 78-89]. The glucan polymers which are in greater abundance than mannan in the *C. albicans* cell wall are immunologically less active [Nelson R. D, Shibata N, Podzorski R. P, Herron M. J. *Candida* mannan: chemistry, suppression of cell-mediated immunity, and possible mechanisms of action. Clin Microbiol Rev, 1991. 4(1): p. 1-19]. Since mannan is a major antigenic component of the cell wall, different chemical and enzymatic methods have been used to extract mannan from *C. albicans*, but these methods have limitations. When mannan is extracted by hot alkali treatment, mannose-serine, and mannose-threonine linkages, phosphodiester linkages and some peptide bonds are cleaved at basic pH. The loss of the O-linked oligosaccharides attached via phosphate groups leaves a modified mannan product that is greatly altered in its antigenicity and biological effects [Nelson R. D, Shibata N, Podzorski R. P, Herron M. J. Candida mannan: chemistry, suppression of cell-mediated immunity, and possible mechanisms of action. Clin Microbiol Rev, 1991. 4(1): p. 1-19]. Hot water extraction may denature the protein structure in mannoproteins. Thus the extraction procedures may modify the mannan product and alter the antigenicity.

Antibody tests have been less useful mainly because anti-*Candida* antibodies are often present in healthy individuals which is considered to be a consequence of immunization from *Candida* in the commensal flora (Odds, F. C., and E. G. Evans. 1980. Distribution of pathogenic yeasts and humoral antibodies to candida among hospital inpatients. J Clin Pathol 33:750-6). Furthermore, the antibody response of *Candida*-infected patients is often impaired by the underlying condition, particularly in non-surgical patients.

The human IgG subclasses differ with respect to physical, chemical, and biological properties. IgG1, IgG2, and IgG3 activate complement, although IgG2 less efficiently. In contrast to IgG1, IgG3, and IgG4, IgG2 demonstrates no or low binding capacity to human mononuclear cells and neutrophils. The subclass distribution of the antibody response is influenced by the nature of the immunogen, the localization of the entry into the body, and age of the host. IgG1 and IgG3 antibodies are mainly induced by protein antigens whereas IgG2 is predominating against polysaccharides (Hammarstrom, L., M. Granstrom, V. Oxelius, M. A. Persson, and C. I. Smith. 1984. IgG subclass distribution of antibodies against *S. aureus* teichoic acid and alpha-toxin in normal and immunodeficient donors. Clin Exp Immunol 55:593-601; Mattsby-Baltzer, I., L. Edebo, B. Jarvholm, B. Lavenius, and T. Soderstrom. 1990. Subclass distribution of IgG and IgA antibody response to *Pseudomonas pseudoalcaligenes* in humans exposed to infected metal-working fluid. J Allergy Clin Immunol 86:231-8; Shakib, F., and D. R. Stanworth. 1980. Human IgG subclasses in health and disease. (A review). Part I. Ric Clin Lab 10:463-79).

DESCRIPTION OF THE INVENTION

One object of the present invention is to provide more native forms of *C. albicans* cell wall antigens which may improve the serological test for identifying patients with candidosis.

The present invention relates to the use of an antibody to a *C. albicans* cell wall antigen, or to a solubilized phosphopeptidomannan (PPM) fraction of the cell wall of *C. albicans*, or preferably a combination of an IgG2 antibody to a phosphopeptidomannan (PPM) fraction of the cell wall of *C. albicans*, and an IgG1 or IgG3 antibody to a *C. albicans* cell wall antigen in the diagnosis of candidiasis or invasive candidiasis.

In view of the above mentioned problems, an attempt was made to prepare native cell wall fragments and to release the phosphopeptidomannan from *C. albicans* cell wall by a gentle method to keep the immunogenic regions more intact. The antibody activity against various *C. albicans* cell wall preparations (cell wall fragments, modified cell wall fragments, phosphopeptidomannan, and β(1-3)(1-6) glucan) was investigated in order to find antigens with high discriminatory power for diagnosis of acute deep *Candida* infection. Rabbit immune sera and sera from patients with candidemia were used for this purpose. The antibody levels were determined by the enzyme linked immunosorbent assay (ELISA).

Serological tests for diagnosis of disseminated fungal infections in the immunocompromised host are used with varying results. In the work leading to the present invention, the discriminatory power of antibodies to *C. albicans* cell wall components was evaluated in order to find antigenic markers for serological diagnosis of candidemia.

Native *C. albicans* cell wall fragments (CW), periodate ($CW_{IO4}$) and proteinase-K ($CW_P$) treated CW, a mildly extracted phosphopeptidomannan (PPM), and β(1-3)(1-6)-glucan were used as antigens in ELISA with sera from rabbits immunized with *C. albicans* (n=10), patients with culture proven candidemia (n=8), and healthy individuals (n=8).

The antibody response in rabbits was predominated by anti-PPM antibodies a finding which was confirmed by inhibition-ELISA. Accordingly, periodate treatment ($CW_{IO4}$) destroyed a major part of the antigenic epitopes. Low rabbit antibody levels were found against glucan, the major *Candida* cell wall component supporting its localization mainly in the inner part of the *C. albicans* cell wall. Somewhat different from the rabbit serum IgG antibody response against PPM, which was at least tenfold higher than against CW, the human IgG antibody levels in patients with candidemia were similar for both antigens, the levels being significantly higher than in the healthy controls (CW, P=0.0005 and PPM, P<0.0001). Although the human anti-glucan and anti-$CW_{IO4}$ IgG antibody levels were overall low, they were still significantly increased in the patient group (P=0.0159 and P=0.0491, respectively). In addition a correlation was noticed between these antibodies. No significant differences were found for IgM antibodies between patients and controls using CW, $CW_{IO4}$, PPM and Glu as antigens. In conclusion, IgG antibodies to PPM and native cell wall fragments (CW) were highly discriminatory for candidemia and thus promising antigen candidates for serodiagnosis.

Sera from a total of 15 patients collected on two to three consecutive occasions starting at the day of culture-proven candidiasis were analyzed by enzyme linked immunosorbent assay (ELISA). Control groups consisted of lactating mothers (n=9, group I) with breast milk positive for *C. albicans* and acute inflammation of the nipples and age-matched blood donors (n=10, group II).

It was shown that within the first three weeks all patients were positive for β(1-3)-glucan (GLUSPECY™), but none for mannan (PASTOREX™ *Candida*). The controls were neither positive for β(1-3)-glucan (<20 pg/ml) nor mannan (<2.5 ng/ml). IgG1 anti-CW and IgG2 anti-PPM antibodies were the most discriminatory antibodies. The IgG1 anti-CW antibodies were partly less sensitive to non-*C. albicans* candidiasis. The ratios of IgG1 anti-CW/IgG2 anti-PPM were significantly lower in non-surviving patients than in the other patients within the first 6 days of candidiasis (P=0.019). IgG2 anti-$CW_{IO4}$ and anti-glucan antibodies correlated strongly (p<0.0001) and a lack of these antibodies were associated with increasing β(1-3)-glucan levels. A high antibody level for IgG1 anti-CW or IgG2 anti-PPM antibodies (≧log 3), or the sum of them (≧log 5) showed a 92% sensitivity and 100% specificity and positive predictive value. In conclusion, β(1-3)-glucan and the two subclass antibodies seem to be early specific markers in the laboratory diagnosis of candidiasis. The kinetics of the β(1-3)-glucan level may also help in evaluating the therapeutic efficacy of antimycotic treatment.

Thus, the present invention relates to the following:

The use of a combination of an IgG2 antibody to a phosphopeptidomannan (PPM) fraction of the cell wall of *C. albicans*, and an IgG1 antibody to a *C. albicans* cell wall antigen, and glucan for the diagnosis of candidiasis or invasive candidiasis.

The use of an antibody, such as an IgG2 antibody, an IgG1 antibody and/or an IgG3 antibody, to a *C. albicans* cell wall antigen or to a solubilized phosphopeptidomannan (PPM) fraction of the cell wall of *C. albicans* for the diagnosis of candidiasis or invasive candidiasis.

A diagnostic kit for the diagnosis of candidiasis or invasive candidiasis comprising
  means for drawing a sample from a patient;
  means for an assay, such as a sandwich ELISA assay, for the detection of a combination of an IgG2 antibody to a phosphopeptidomannan (PPM) fraction of the cell wall of *C. albicans*, and an IgG 1 antibody to a *C. albicans* cell wall antigen, and glucan, wherein said sample is analyzed for the presence of the simultaneous presence of an IgG2 antibody to a phosphopeptidomannan (PPM) fraction of the cell wall of *C. albicans*, and an IgG 1 antibody to a *C. albicans* cell wall antigen, and glucan.

Diagnostic kit for the diagnosis of candidiasis or invasive candidiasis comprising
  means for drawing a sample from a patient;
  means for an assay, such as a sandwich ELISA assay, for the detection of an antibody, such as an IgG2 antibody, an IgG1 antibody and/or an IgG3 antibody, to a *C. albicans* cell wall antigen or to a solubilized phosphopeptidomannan (PPM) fraction of the cell wall of *C. albicans*, wherein said sample is analyzed for the presence of an antibody to a *C. albicans* cell wall antigen or to a solubilized phosphopeptidomannan (PPM) fraction of the cell wall of *C. albicans*.

A method for diagnosing candidiasis or invasive candidiasis a patient comprising
  drawing a sample from the patient, and
  performing an assay for the detection of an IgG2 antibody to a phosphopeptidomannan (PPM) fraction of the cell wall of *C. albicans*, and an IgG1 antibody to a *C. albicans* cell wall antigen, and glucan,
wherein the simultaneous presence of an IgG2 antibody to a phosphopeptidomannan (PPM) fraction of the cell wall of *C. albicans*, and an IgG1 antibody to a *C. albicans* cell wall antigen, and glucan indicates candidiasis or invasive candidiasis in the patient A method for diagnosing candidiasis or invasive candidiasis a patient comprising
  drawing a sample from the patient, and
  performing an assay for the detection of an antibody to a *C. albicans* cell wall antigen or to a solubilized phosphopeptidomannan (PPM) fraction of the cell wall of *C. albicans*,
wherein the presence of an antibody to a *C. albicans* cell wall antigen or to a solubilized phosphopeptidomannan (PPM) fraction of the cell wall of *C. albicans* indicates candidiasis or invasive candidiasis in the patient.

The use of an antibody, such as an IgG antibody to a native cell wall fragment of *C. albicans* and/or an IgG antibody to a solubilized phosphopeptidomannan (PPM) fraction of the cell wall of *C. albicans*, preferably a human serum IgG antibody, for the diagnosis of candidemia or invasive *Candida* infection.

Diagnostic kit for the diagnosis of candidemia or invasive *Candida* infection comprising
  means for drawing a sample from a patient;
  means for an assay, such a sandwich ELISA assay, for the detection of an IgG antibody, such as a human serum IgG antibody, to a native cell wall fragment of *C. albicans* or an IgG antibody to a solubilized phosphopeptidomannan (PPM) fraction of the cell wall of *C. albicans*, wherein said sample is analyzed for the presence of an IgG antibody to a native cell wall fragment of *C. albicans* or an IgG antibody to a solubilized phosphopeptidomannan (PPM) fraction of the cell wall of *C. albicans*.

A method for diagnosing candidemia or invasive *Candida* infection in a patient comprising
  drawing a sample from the patient, and
  performing an assay for the detection of an IgG antibody, such as a human serum IgG antibody, to a native cell wall fragment of *C. albicans* or an IgG antibody to a solubilized phosphopeptidomannan (PPM) fraction of the cell wall of *C. albicans*,
wherein the presence of an IgG antibody to a native cell wall fragment of *C. albicans* or an IgG antibody to a solubilized phosphopeptidomannan (PPM) fraction of the cell wall of *C. albicans* indicates candidemia or invasive *Candida* infection in the patient.

The invention will now be further explained in the following examples. These examples are only intended to illustrate the invention and should in no way be considered to limit the scope of the invention.

BRIEF DESCRIPTION OF THE DRAWINGS

In the examples, reference is made to the accompanying drawings on which.

EXPERIMENTAL

Part I

Materials and Methods

Antigens

*C. albicans* (strain ATCC 64549) serotype A was grown in Sabourad dextrose broth on a shaker at 37° C., for 24 h. Yeast cells were obtained from the culture medium by centrifugation. The antigenic factors 4, 5 and 6 were expressed by the yeast cells as determined by *Candida* Check (Iatron laboratories, Japan), an agglutination test using rabbit polyclonal antibodies directed to factor 4, 5 and 6.

Formalinized yeast cells were used for immunization of rabbits. Thus, cells were suspended in formaldehyde (5%) and kept at r.t. overnight. The cells were washed two times with distilled water and once with PBS. Before the cells were lyophilized the killing efficiency was checked by culturing.

Figure 1:
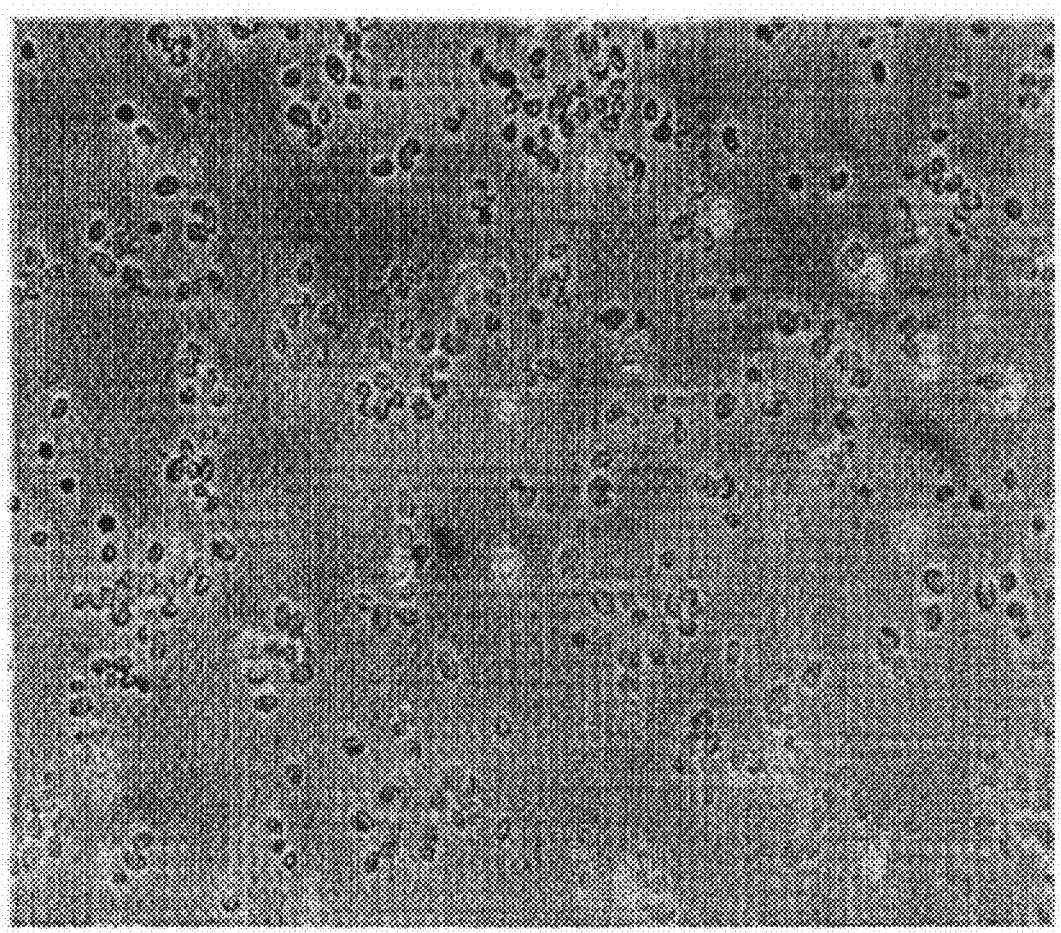
FIG. 1 is a microphotograph of *C. albicans* yeast cells treated with glass beads (phase contrast microscopy, magnification 500). Dead cells are presented by dark empty sacs, while whole yeast cells appear with bright centers.

Cell wall fragments of *C. albicans* (CW). After repeated washings of the cultivated cells, the cell pellet was suspended in an equal volume of distilled water. Glass beads (0.5 mm in diameter) were added to the cell suspension in a volume ratio of 1:3. The mixture was shaken repeatedly (20 cycles) in a vortex mixer for one minute with intervals on ice. The supernatant was collected and the glass beads were washed several times with distilled water, till the washing solution became clear. The supernatant and washing solutions were pooled. The cell wall fraction was sedimented at 1200×g for 10 min and washed 10 times with ice-cold distilled water. Almost complete cell breakage (90-95%) was obtained as assessed by phase-contrast microscopy (FIG. 1). The CW suspension was washed three times with distilled water and freeze-dried.

Modified CW. CW was treated with sodium periodate in order to destroy the carbohydrate structures by oxidation. To 16 mg of lyophilized CW suspended in 5 ml of 0.1M sodium phosphate buffer (pH 6) was added 0.5 ml of 0.15 M NaIO$_4$ [Quash G, Roch A. M, Niveleau A, Grange J, Keolouangkhot T, Huppert J. The preparation of latex particles with covalently bound polyamines, IgG and measles agglutinins and their use in visual agglutination tests. J Immunol Methods, 1978. 22(1-2): p. 165-74]. The mixture was left at 4° C. in the dark for 3 h. The reaction was stopped by adding 0.6 ml of 0.15 M Na$_2$SO$_3$. After 30 min, the mixture was dialyzed against 0.1 M phosphate buffer pH 6, at 4° C. overnight. The buffer was changed several times to remove low molecular weight oxidation products. Finally the CW was dialyzed against distilled water. The periodate treated CW suspension (CW$_{IO4}$) was lyophilized.

CW was also treated with proteinase K, in order to reduce the protein content. Lyophilized CW (20 mg/ml) was incubated with proteinase K (final concentration 2 mg/ml) (Sigma, USA), at 37° C. for 3 h [Hitchcock P. J, Brown T. M. Morphological heterogeneity among *Salmonella* lipopolysaccharide chemotypes in silver-stained polyacrylamide gels. J Bacteriol, 1983. 154(1): p. 269-77]. Thereafter the enzyme was heat-inactivated by incubation at 70° C. for 30 min. The suspension was washed three times with distilled water and finally dialyzed at 4° C. overnight. The dialysate (CW$_P$) was lyophilized.

Phosphopeptidomannan (PPM). PPM was extracted by a method used by Lloyd with *Cladosporium werneckii* [Lloyd K. O. Isolation, characterization, and partial structure of peptido galactomannans from the yeast form of *Cladosporium werneckii*. Biochemistry, 1970. 9(17): p. 3446-53]. Freeze-dried *C. albicans* yeast cells (11 g) were suspended in 110 ml of 0.05 M potassium phosphate buffer (pH 7.0) and heat-treated at 100° C. for 2 hr. After cooling the extract was fractionated with 0.22 g of hexadecyltrimethylammonium bromide (Cetavlon) at pH 8.8, in the presence of 6.1 ml of boric acid (1%). The precipitate was centrifuged and washed with 0.5% sodium borate (pH 8.8). The residue was dissolved in 2% acetic acid (3.1 ml) and sodium acetate (0.06 g). Ethanol (3 volumes) was added to the solution. The resulting precipitate was removed by centrifugation and washed with 2% acetic acid in ethanol followed only by ethanol. The product was lyophilized and yielded 0.108 g (1%) of material. The PPM was highly water soluble.

PPM was further characterized by SDS polyacrylamide gel electrophoresis (3-8% gradient gel, Invitrogen life technologies, USA). PPM was mixed in sample buffer (NUPAGE™ sample buffer, Invitrogen) and heat treated at 70° C. for 10 min prior to application onto the gel. The gels were stained for protein by Silver Stain Plus (BIORAD, USA) and for carbohydrate by the periodic acid-Schiff (PAS) method [Kapitany R. A., Zebrowski E. J. A high resolution PAS stain for polyacrylamide gel electrophoresis. Anal Biochem, 1973. 56(2): p. 361-9].

Degradation of PPM with acid and alkali. In order to characterize acid and/or alkali-labile epitopes, PPM was treated with HCl and NaOH as described by Kobayashi et. al [Kobayashi H, Matsuda K, Ikeda T, Suzuki M, Takahashi S, Suzuki A, Shibata N, Suzuki S. Structures of cell wall mannans of pathogenic *Candida tropicalis* IFO 0199 and IFO 1647 yeast strains. Infect Immun, 1994. 62(2): p. 615-22]. PPM was dissolved in 10 mM HCl in a final concentration of 9 mg/ml and incubated at 100° C. for 1 h as described by Kobayashi [Kobayashi H, Matsuda K, Ikeda T, Suzuki M, Takahashi S, Suzuki A, Shibata N, Suzuki S. Structures of cell wall mannans of pathogenic *Candida tropicalis* IFO 0199 and IFO 1647 yeast strains. Infect Immun, 1994. 62(2): p. 615-22]. The solution was neutralized with 100 mM NaOH. The acid treated PPM was designated PPM$_{HCl}$. For alkali treatment, the PPM was dissolved in 100 mM NaOH at a final concentration of 6.7 mg/ml. The resultant solution was kept at 25° C. for 18 h and thereafter neutralized with 1 M HCl [Kobayashi H, Matsuda K, Ikeda T, Suzuki M, Takahashi S, Suzuki A, Shibata N, Suzuki S. Structures of cell wall mannans of pathogenic *Candida tropicalis* IFO 0199 and IFO 1647 yeast strains. Infect Immun, 1994. 62(2): p. 615-22]. The alkali treated PPM was designated PPM$_{NaOH}$.

Glucan (Glu). Glu prepared from *Saccharomyces cerevisiae* (Sigma, St Louis), barley (Glu-B), and *Alcaligenes faecalis* (Glu-C) was used. Glu consists of β(1-3)(1-6)-D-linked glucose residues, which is also a component of *C. albicans* glucan [Kapteyn J. C, Montijn R. C, Dijkgraaf G. J, Van den Ende H, Klis F. M. Covalent association of beta-1, 3-glucan with beta-1,6-glucosylated mannoproteins in cell walls of *Candida albicans*. J Bacteriol, 1995. 177(13): p. 3788-92; Sanjuan R., Zueco J, Stock R, Font de Mora J, Sentandreu R. Identification of glucan-mannoprotein complexes in the cell wall of *Candida albicans* using a monoclonal antibody that reacts with a (1,6)-beta-glucan epitope. Microbiology, 1995. 141(Pt 7): p. 1545-51; Smits G. J, Kapteyn J. C, van den Ende H, Klis F. M. Cell wall dynamics in yeast. Curr Opin Microbiol, 1999. 2(4): p. 348-52]. Glu-B consists of β(1-4)(1-6)-D-linked glucose residues. Glu-C consists entirely of β(1-3)-D-linked glucose residues. Glu and Glu-C, which are insoluble in water, were solubilized in 0.1 M NaOH at a concentration of 10 mg/ml. These solutions were then used for chemical analyses.

Mannan (Man). Mannan of *C. albicans* ATCC 64549 was prepared in accordance with the description of Kocourek and Ballou [Kocourek J, Ballou C. E. Method for fingerprinting yeast cell wall mannans. J Bacteriol, 1969. 100(3): p. 1175-81]. Briefly, mannan was extracted in 0.02 M citrate buffer (pH 7.0) at 125° for 90 min, followed by precipitation with Fehling solution. The copper complex was dissolved in 3 M HCl, and precipitated with methanol-acetic acid, then washed with ethanol and ethyl-ether. The product was air dried.

This antigen was prepared in order to compare the commonly used mannan extraction procedure with that of PPM.

Determination of Protein, Hexose and Phosphate

The protein content of the various antigens was determined by a colorimetric method. A set of standard protein concentrations was prepared by diluting a stock solution of bovine serum albumin (BSA). The standard solution, blank, and unknown samples (CW, $CW_p$, $CW_{IO4}$, PPM, Man, Glu, Glu-B, and Glu-C) were added in 50 µl volumes to the wells of a microtiter plate. The bi-cinchoninic acid protein assay reagent, BCA (Pierce, USA) was added to each well (200 µl). The solutions in the wells were allowed to mix for 30 sec. The plate was incubated at 37° C. for 45 min. The absorbance was read at 560 nm. The standard curve was plotted and the protein concentrations determined for each sample.

Hexose was determined by the colorimetric method of Dubios et al. with mannose and glucose as standards [Dubios M, Gilles K. A, Hamilton J. K, Robers P. A, Smith S. Colorimetric method for determination of sugars and related substances. Anal. Chem., 1956. 28: p. 350-356].

The phosphate was determined by the method described by Ames et al. with some modifications [Ames B. N., Dubin D. T. The role of polyamines in neutralization of bacteriophage deoxyribonucleic acid. J. Bacteriol. Chem., 1960. 235(3): p. 769-775].

Antibodies to *C. albicans*

Rabbit antiserum. Antiserum to *C. albicans* was prepared by immunizing ten New Zealand white rabbits (2-3 kg) with i.v. injections of 200 µl of formalin-killed *C. albicans* (1 mg/ml, two rabbits) or *C. albicans* CW (1 mg/ml) dissolved in PBS. The animals were immunized twice a week for eight weeks. The rabbits were bled once a week prior to the injection of *C. albicans*. One week after the last immunization the rabbits were exsanguinated by heart puncture. Serum was stored frozen. A pool of all ten antisera was prepared.

Sera from patients with candidemia. Sera from patients with candidemia were analyzed for antibody activity against CW, PPM, and Glu by ELISA. Healthy blood donors constituted the control group. The mean age of the patient and control group was 65±14 and 59.5±4, respectively. The sera were collected from the patients approximately one week after the blood culturing. All patients were on flucytosine treatment at the time of blood sampling.

Enzyme-Linked Immunosorbent Assay, ELISA

Microplates (Nunc immunoplate, Denmark) were coated with 100 µl of a suspension of CW, PPM, Man or Glu, diluted in 50 mM $Na_2CO_3$ buffer, pH 9.3. The CW antigen was sonicated prior to coating in order to disaggregate the cell wall fragments which made the solution clearer. Optimal coating concentrations of CW, PPM, Man and Glu were determined by using the pool of rabbit antiserum diluted to 1/1000. Optimal concentrations were reached at 50, 5, 5 and 20 mg/ml of CW, PPM, Man and Glu, respectively. The plates were incubated at room temperature for 2 h, and thereafter kept at 4° C. overnight. After rinsing the plates once with PBS, 100 µl of blocking buffer (1% w/v BSA, 0.05% TWEEN™ 20 in PBS) were added to each well and incubated for 1 h at room temperature. The plates were rinsed once with 0.05% TWEEN™ 20 in PBS (PBS-T). Rabbit or human serum diluted in tenfold serial steps (1/100-1/10000) in PBS-T, was added to the wells (100 µl) in duplicates and incubated for 2 h at room temperature. After rinsing the plates three times with PBS-T, 100 µl of alkaline phosphatase-conjugated goat anti-rabbit or goat anti-human IgM or IgG were added to the wells. The conjugated anti-rabbit antibodies (Southern Biotechnology Associates, USA) were used at dilutions of 1/1000. The conjugated anti-human IgG and IgM (Jackson ImmunoResearch Laboratories, USA) were used in concentrations of 0.6 µg/ml. After incubation at room temperature for 2 h followed by rinsing, 100 µl of paranitrophenylphosphate (1 mg/ml, Sigma) diluted in diethanolamine buffer (pH 9.8) were added to each well. The absorbance was read at 405 nm after a suitable color intensity had developed.

Inhibition Assay

Increasing amounts of CW, $CW_{IO4}$, $CW_p$, PPM, Man, or the various glucans (0.1-1000 µg/ml) were added to series of tubes containing a constant amount of rabbit immune serum. The solutions were incubated at 37° C. for 30 min and thereafter at 4° C. overnight. The solutions were centrifuged to remove any precipitation, and the supernatants were analyzed for the remaining antibody activity using CW, Glu, and PPM as coating antigens. The pool of rabbit immune serum diluted 1/500 (Glu) or 1/2000 was used for the inhibition assay. The inhibition capacity of an antigen was defined as the concentration needed for inhibiting the antibody activity to 50%, i.e. reducing the absorbance value to 50% of that of the unabsorbed serum dilution ($EI_{50}$) [Mattsby-Baltzer I, Mielniczuk Z, Larsson L, Lindgren K, Goodwin S. Lipid A in *Helicobacter pylori*. Infect Immun, 1992. 60(10): p. 4383-7].

Results

Characterization of Antigens

The hexose, protein and phosphate contents of CW, $CW_{IO4}$, $CW_p$, PPM, Man, and the glucans are shown in table 1 $CW_{IO4}$ contained the lowest and highest amount of carbohydrate and protein, respectively. This was expected since periodate treatment oxidises aldehyde groups of carbohydrates [Kanbe T, Morishita M, Ito K, Tomita K, Utsunomiya K, Ishiguro A. Evidence for the presence of immunoglobulin E antibodies specific to the cell wall phospho-mannoproteins of *Candida albicans* in patients with allergies. Clin Diagn Lab Immunol, 1996. 3(6): p. 645-50]. The proteinase treatment reduced the protein content to approximately 50% of that in CW. PPM contained 10% protein and 0.83% phosphate. The phosphate content of PPM was approximately 3 and 500 times higher than in CW and Man respectively. PPM contained 4 times more protein than Man.

SDS-PAGE of PPM revealed a major part of PAS positive material above a molecular weight of 200 kD. Two bands (approximately 48 and 36 kD) were observed by protein staining (not shown).

Specificity of Rabbit Antibodies to *C. albicans*

Figure 2:
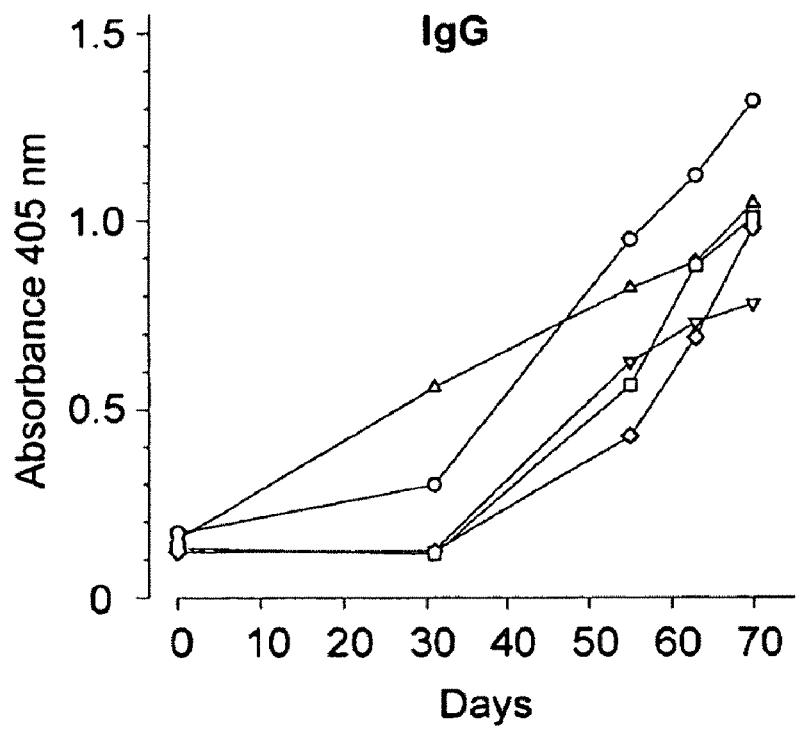
FIG. 2 illustrate. IgG and IgM antibodies to CW in five rabbits immunized with formalin killed yeast cells ($\sigma, \lambda$) and CW ($\nu, \upsilon, \iota$) as analyzed by ELISA. Serum samples were also collected before the start of immunization (day 0). The antibody concentrations are expressed as the absorbance value at a serum dilution of 1/1000.
Figure 2:
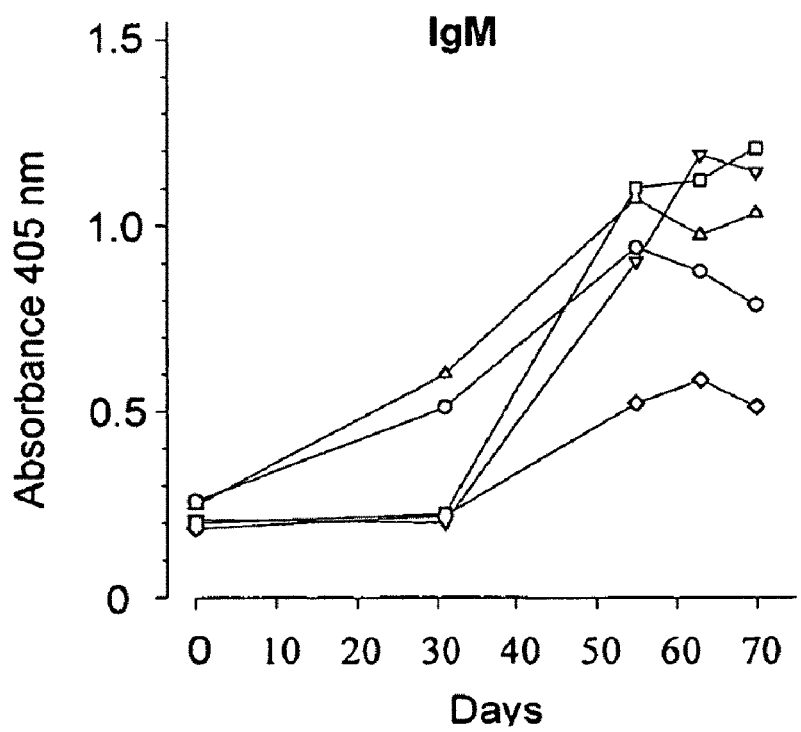

The IgG and IgM antibody responses to CW were analyzed in all immunized rabbits. The antibody response pattern was almost the same for all rabbits (only five rabbits shown in FIG. 2). The rabbits immunized with whole yeast cells showed an earlier response. The preimmune sera of the rabbits showed no or low antibody levels.

Figure 3:
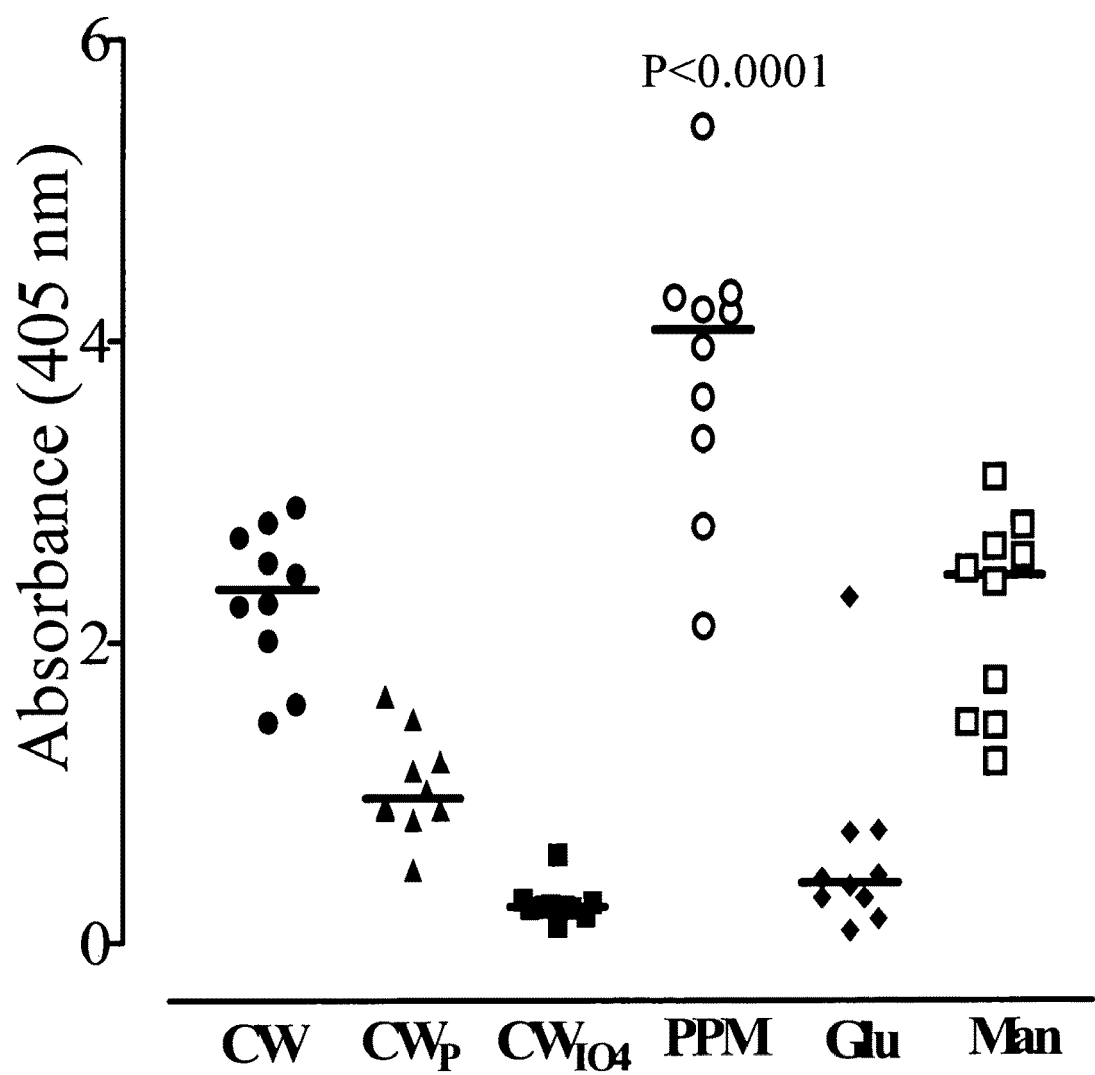
FIG. 3 illustrates rabbit IgG anti-*C. albicans* antibodies analyzed by ELISA using CW, $CW_p$, $CW_{IO4}$, PPM, Glu and Man as antigens. The sera were analyzed at a dilution of 1/100.

The specificity of the antibodies was further investigated by using CW, $CW_p$, $CW_{IO4}$, PPM, Man and Glu as antigens (FIG. 3). The highest IgG antibody levels were observed with PPM. The anti-PPM antibodies correlated significantly only with the anti-CW antibodies (P=0.023). The IgG antibody activity was higher against Man and CW than against the modified CW antigens or Glu. The anti-CW antibodies correlated significantly with the antibodies against proteinase or periodate treated CW (P=0.010, and 0.028 respectively). The anti-mannan antibodies did not correlate with any other antibody. The lowest antibody activity was found against Glu and $CW_{IO4}$. These antibodies were strongly correlated (P<0.0001). No IgG antibody activity was observed in the preimmune-sera against the various antigens except for Glu. All rabbits except one showed low anti-Glu antibody activity before the immunization (not shown).

Figure 4A:
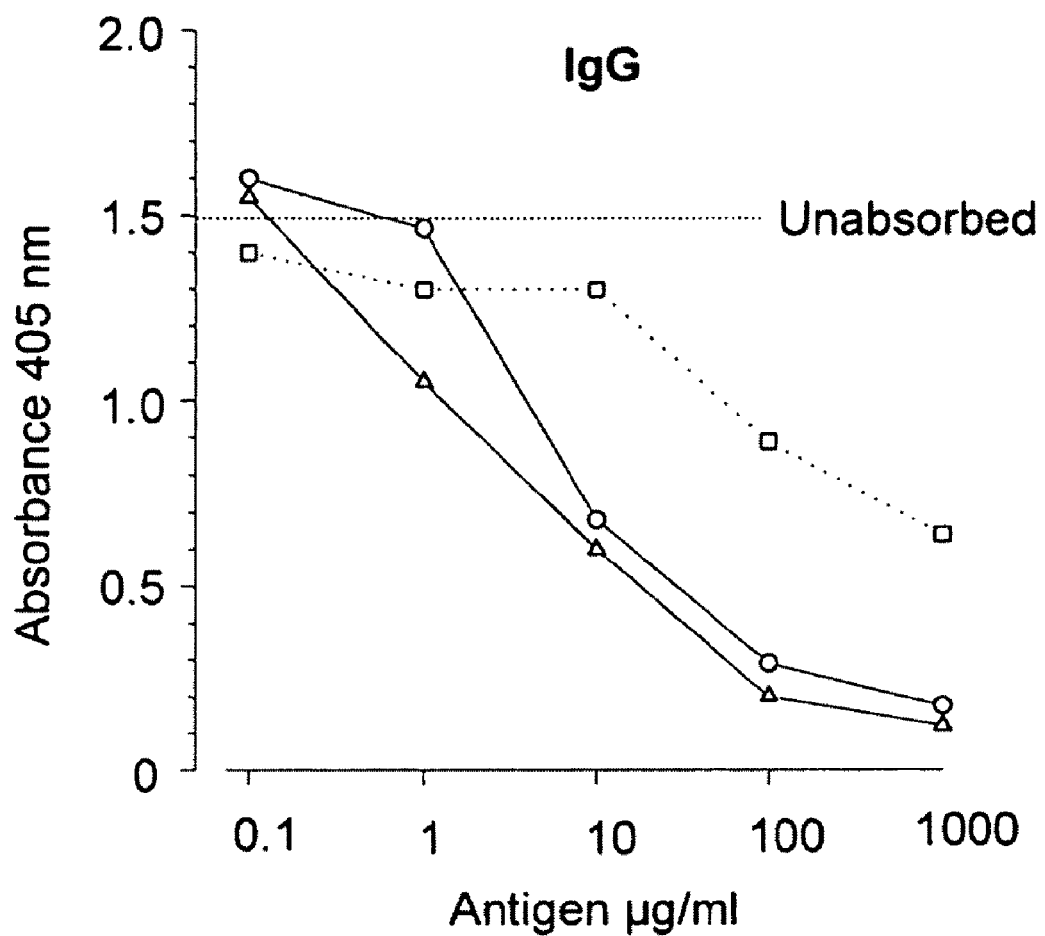
FIGS. 4*a* and 4*b* illustrate how the rabbit serum pool (dilution 1/2000) was absorbed with varying concentrations of antigens and analyzed for remaining IgG and IgM antibody activities against CW. Absorption was performed with CW ( ), $CW_{IO4}$(⁌) and $CW_F$( ). The antibody activity of the unabsorbed serum pool is indicated.
Figure 4B:
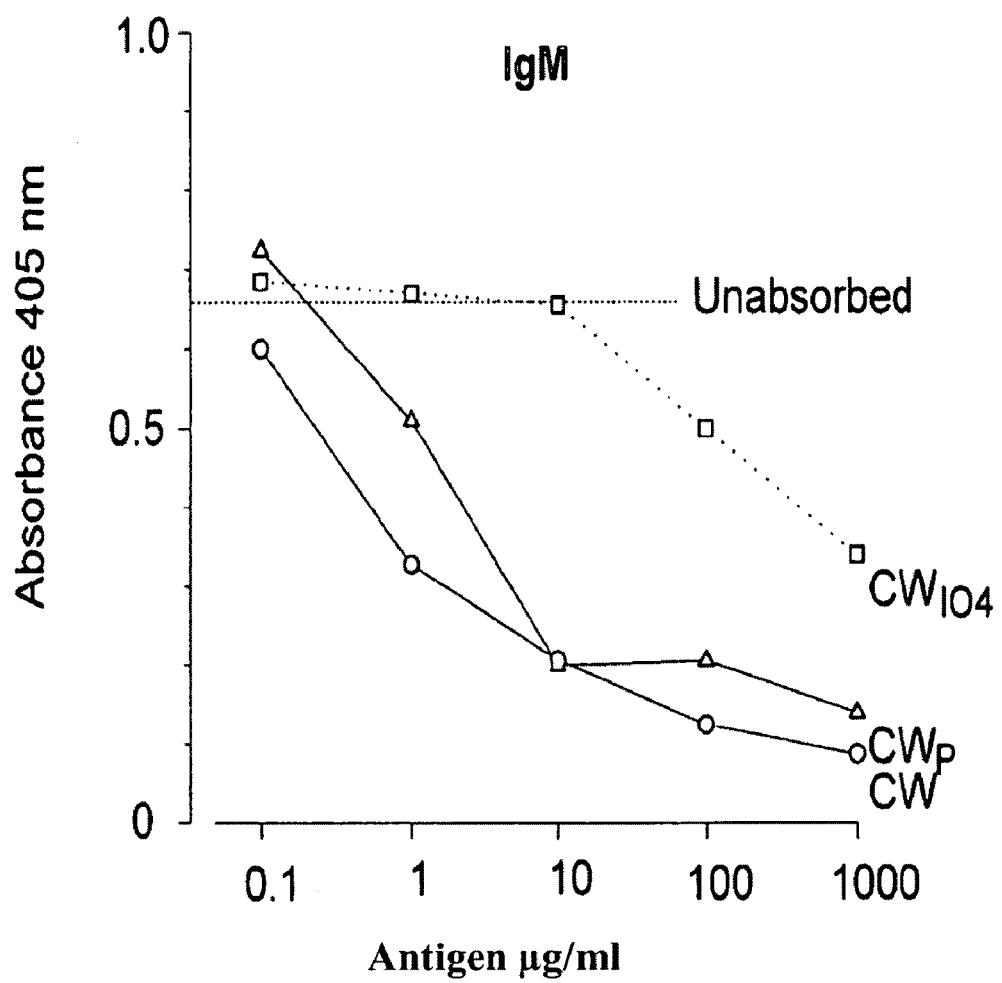

Differences in antibody activity against the varying antigens could partly have originated from variations in the binding of the antigens to the microplate, while still expressing similar or identical antigen epitopes. Therefore cross-reactions between the CW preparations, PPM, Man, and Glu were studied by ELISA inhibition. The pool of rabbit immune serum was absorbed by CW, $CW_{IO4}$, and $CW_p$ and the remaining antibody activity was analyzed by ELISA using CW as antigen (FIGS. 4a and 4b). $EI_{50}$ for $CW_{IO4}$ was 500 (794 µg/ml) and 50 times (251 µg/ml) higher for IgM and IgG respectively, compared with the homologous CW antigen (1.6 and 5.4 µg/ml for IgM and IgG, respectively). Thus periodate treatment of CW reduced the number of antigenic epitopes. The $EI_{50}$ for $CW_p$ was three times higher for IgM and approximately the same for IgG (4 and 5 µg/ml, respectively) in comparison with the homologous antigen, indicating minor influence on antigen epitopes (FIGS. 4a and 4b).

The proportion of anti-CW antibodies directed against PPM, Man, and Glu was analyzed by absorbing the pooled rabbit immune serum with the carbohydrate antigens (table 2). $EI_{50}$ for Glu was approximately 1400- and 16 000 times higher for IgG and IgM compared with PPM. The corresponding figures for Man were 5000 and 4000 times. These results showed that the anti-CW antibodies mainly consisted of antibodies to PPM and Man and to a much lesser extent to Glu. Glu-C inhibited the anti-CW IgG antibody activity at 4.5 times higher concentration than needed for Glu.

The IgG antibody activity to Glu after absorption with the homologous antigen, CW, PPM, Man, Glu-B, and Glu-C was also analyzed (Table 3). $EI_{50}$ was 22 and 28 higher for PPM and CW, respectively, compared with Glu. No inhibition was obtained with Man, Glu-B or Glu-C.

Regarding anti-PPM antibodies, Man and CW inhibited the IgG antibody activity to 50% by a concentration 2 and 35 times of that of PPM respectively, while Glu could not inhibit the antibodies (Table 4).

The changes in antigenic activity of PPM treated by acid or alkali, were compared with the untreated PPM. The $EI_{50}$ values for $PPM_{HCl}$ and $PPM_{NaOH}$ were five- and twofold increased compared with untreated PPM.

Antibodies to CW, PPM and Glu in Sera from Patients with Candidemia

Figure 5:
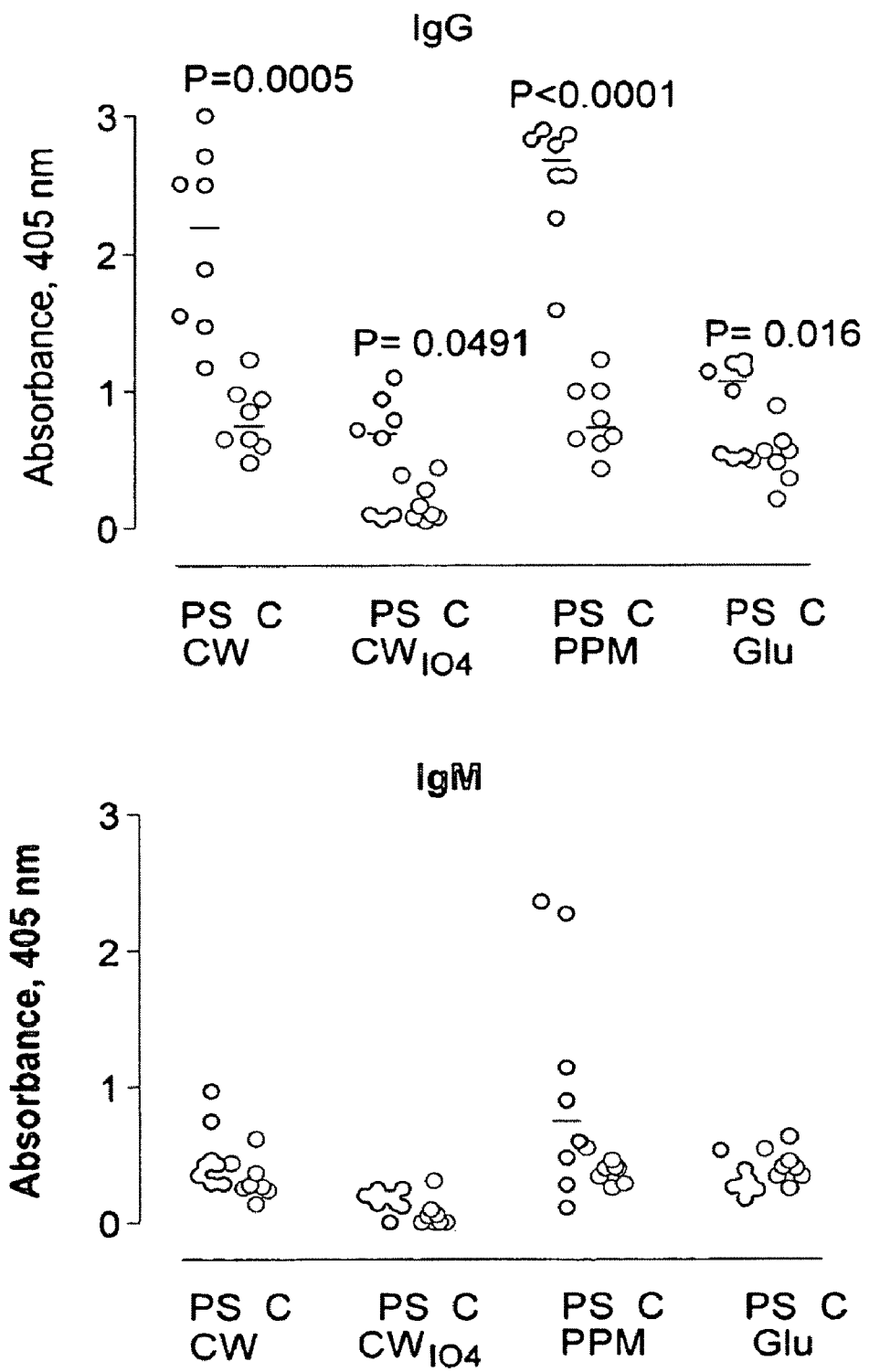
FIG. 5 illustrates serum IgG and IgM antibodies to CW, $CW_{IO4}$, PPM, and Glu in patients with culture-proven candidiasis (PS) and healthy blood donors (C) as analyzed by ELISA. Median values for each group are presented. Statistical comparison was performed with Welch t test.

Sera from patients with candidemia were compared with the sera from healthy blood donors regarding IgG and IgM antibodies to CW, $CW_{IO4}$, PPM and Glu (FIG. 5). The patients showed significantly increased levels of IgG antibodies to all antigens compared with the control group. The IgG anti-PPM antibody levels showed the greatest difference between the two groups with all patient sera showing higher antibody levels than all the reference sera. The IgG antibody activity against $CW_{IO4}$ and Glu were low in both patients and controls. Highly significant correlations were established between CW and the other antigens (Pearson correlation, P<0.0001). In contrast to the rabbit anti-CW IgG antibodies the human anti-CW IgG antibodies were highly correlated to the anti-Glu antibodies. Also in humans the anti-$CW_{IO4}$ IgG antibodies correlated strongly with anti-Glu antibodies p<0.0001). No significant differences were established between the two groups for IgM antibodies.

Discussion

Human serum IgG antibodies to solubilized PPM or as a native cell wall constituent showed the strongest difference regarding patients with candidemia and healthy controls. Also IgG antibodies to $CW_{IO4}$ and Glu were discriminatory. No significantly increased IgM antibody levels were observed for any of the antigens suggesting that the C. albicans infection was not a first time challenge. Most probably the patients had been exposed to Candida earlier in life. As a consequence antibody tests using agglutination would tend to be undiscriminatory, since IgM has much stronger agglutinating capacity than IgG.

PPM, constituted the predominating antigen in the C. albicans cell wall according to the antibody analysis of both rabbit immune sera and human sera. The inhibition ELISA revealed no other antigenic cell wall components of significance in the native cell wall except for Man, which could be regarded as a chemically stripped form of PPM. Thus, the location and abundance of mannoprotein in the outermost layer of the cell wall, is concurrent with high immunogenicity [Nelson R. D, Shibata N, Podzorski R. P, Herron M. J. Candida mannan: chemistry, suppression of cell-mediated immunity, and possible mechanisms of action. Clin Microbiol Rev, 1991. 4(1): p. 1-19; Fradin C, Poulain D, Jouault T. beta-1,2-linked oligomannosides from Candida albicans bind to a 32-kilodalton macrophage membrane protein homologous to the mammalian lectin galectin-3. Infect Immun, 2000. 68(8): p. 4391-8; Gemmill T. R, Trimble R. B. Overview of N- and O-linked oligosaccharide structures found in various yeast species. Biochim Biophys Acta, 1999. 1426(2): p. 227-37].

The reported temperature-dependent disappearance of surface antigenic factors 4, 5, and 6 in C. albicans NIH A-207 was not observed with C. albicans strain used by the inventors grown at 37° C. [Okawa Y, Takahata T, Kawamata M, Miyauchi M, Shibata N, Suzuki A, Kobayashi H, Suzuki S. Temperature-dependent change of serological specificity of Candida albicans NIH A-207 cells cultured in yeast extract-added Sabouraud liquid medium: disappearance of surface antigenic factors 4, 5, and 6 at high temperature. FEBS Lett, 1994. 345(2-3): p. 167-71]. Possible explanations could be that different strains behave somewhat differently or that the growth media are not identical. Whether such surface antigen changes take place in vivo is not known.

Most immunodiagnostic methods available for routine purposes are based on the mannan component of the Candida cell wall. Different methods have been used for preparation of large amounts of mannan including extraction with alkali, citrate buffer or water at temperatures of 100 to 140° C. [Kocourek J, Ballou C. E. Method for fingerprinting yeast cell wall mannans. J Bacteriol, 1969. 100(3): p. 1175-81, Funayama M, Nishikawa A, Shinoda T, Suzuki M, Fukazawa Y. Antigenic relationship between Candida parapsilosis and Candida albicans serotype B. Microbiol Immunol, 1984. 28(12): p. 1359-71; Peat S., Whelan W. J, Edwards. T. E. Polysaccharide of the baker's yeast. Part IV. Mannan. J. Chem. Soc. (London), 1961: p. 29-34; Shibata N, Ichikawa T, Tojo M, Takahashi M, Ito N, Okubo Y, Suzuki S. Immunochemical study on the mannans of Candida albicans NIH A-207, NIH B-792, and J-1012 strains prepared by fractional precipitation with cetyltrimethylammonium bromide. Arch Biochem Biophys, 1985. 243(2): p. 338-48]. Extracted mannan has been separated from other components by precipitation. The solution of Fehling as originally described by Peat et. al. has been used for this purpose in most serological investigations, although this method has disadvantages [Sendid, B, Tabouret M., Poirot J. L, Mathieu D, Fruit J, Poulain D. New enzyme immunoassays for sensitive detection of circulating *Candida albicans* mannan and antimannan antibodies: useful combined test for diagnosis of systemic candidiasis. J Clin Microbiol, 1999. 37(5): p. 1510-7; Meckstroth K. L, Reiss E, Keller J. W, Kaufman L. Detection of antibodies and antigenemia in leukemic patients with candidiasis by enzyme-linked immunosorbent assay. J Infect Dis, 1981. 144 (1): p. 24-32; Lehmann P. F, Reiss E. Comparison by ELISA of serum anti-*Candida albicans* mannan IgG levels of a normal population and in diseased patients. Mycopathologia, 1980. 70(2): p. 89-93; Au-Young J. K, Troy F. A, Goldstein E. Serologic analysis of antigen-specific reactivity in patients with systemic candidiasis. Diagn Microbiol Infect Dis, 1985.3(5): p. 419-32]. The alkaline pH of Fehling's solution modifies the structure of the mannan by cleaving the mannose-serine and mannose-threonine linkages and some peptide bonds. That alkaline pH modifies the antigen was supported by the increased $EI_{50}$ value of $PPM_{NaOH}$ with respect to untreated PPM (table 4). Another disadvantage is that a considerable amount of copper remains bound to the mannan, even after washing the product several times [Nelson R. D, Shibata N, Podzorski R. P, Herron M. J. *Candida* mannan: chemistry, suppression of cell-mediated immunity, and possible mechanisms of action. Clin Microbiol Rev, 1991. 4(1): p. 1-19].

In the study leading to the present invention, PPM was extracted by a very mild method using phosphate buffer (pH 7.0) and a temperature not exceeding 100° C., followed by Cetavlon precipitation. By using Cetavlon, linkages sensitive to cleavage at an alkaline pH were preserved. PPM contained 10% protein and almost 1% phosphate, which was 4- and 400-fold higher compared with the respective concentrations in Man. Based on these chemical data, together with a higher anti-*C. albicans* antibody activity against PPM than against Man in ELISA, a different pattern of the inhibitory activity of PPM compared with Man in inhibition-ELISA, and the significant correlation of anti-PPM to anti-CW antibodies, the preparation procedure according to the invention for PPM appeared to better retain antigenic determinants than the extraction procedure for Man (FIG. 3, Table 1-4). Possibly critical structures such as phosphodiester linkages and peptide bonds were left more intact in immunodominant portions of PPM.

The presence of the charged phosphate groups in the outer region of the wall has effects not only on the attraction or attachment of yeast cells to other surfaces, but probably also on the antigenicity. The anionic sites on developing germ tubes are believed to be formed by the negatively charged phosphate groups [Reiss E., Hearn V. M, Poulain D, Shepherd M. G. *Structure and function of the fungal cell wall. J Med Vet Mycol*, 1992. 30(Suppl 1): p. 143-56]. It has been shown that mutant strains of *C. albicans*, which lacked the mannosyl-α-phosphoryl and mannosyl-α1-6-linkages, escaped agglutination by a rabbit polyclonal antiserum, raised against *C. albicans* blastoconidia [Whelan W. L, Delga J. M, Wadsworth E, Walsh T. J, Kwon-Chung K. J, Calderone R, Lipke P. N. Isolation and characterization of cell surface mutants of *Candida* albicans. Infect Immun, 1990. 58(6): p. 1552-7]. The results suggest that the phosphate groups and the ester-bound side chains are important for antibody recognition. Thus, mannan purification methods that break up such linkages could be detrimental to the antigen determinants.

Reduction of the protein content in CW, approximately to 50% (Table 1), did not significantly change the antigenicity of CW (FIGS. 4a and 4b). The modification probably reduced the absorption of the antigen to the microtiter plate (FIG. 3), since lower antibody activity was observed against it than against untreated CW, whereas it retained almost identical capacity as CW to absorb anti-CW antibodies. Periodate oxidation of CW diminished the antibody activity significantly, probably as a consequence of reduction in carbohydrate content and further modifications of antigenic epitopes. The strong correlation of both human and rabbit IgG anti-$CW_{IO4}$ with anti-glucan antibodies indicated that common epitopes occur in both types of preparations, most probably β(1-3)(1-6) glucan.

Anti-mannan antibodies are widely and normally found in human sera [Jones J. M. Quantitation of antibody against cell wall mannan and a major cytoplasmic antigen of *Candida* in rabbits, mice, and humans. Infect Immun, 1980. 30(1): p. 78-89]. Faux et. al. reported that 76% of an adult blood donor population had specific antibodies to mannan, and that the most frequent anti-mannan antibody was of the IgG class determined by ELISA [Faux J. A, Agbarakwe A. E, Misbah S. A, Chapel H. M. A comparison of specific IgG antibody levels to the cell wall mannan of *Candida albicans* in normal individuals and in patients with primary antibody deficiency. J Immunol Methods, 1992. 153(1-2): p. 167-72]. The method for extracting the mannan antigen was, however, not described. In our study all control sera showed IgG antibody activity to PPM and the PPM-containing native CW. However, the levels of antibody to PPM were significantly increased in the patient group. These results are in agreement with the study of Greenfield et. al. who reported that IgG antibodies to mannan (extracted according to Peat et. al.) in ELISA were increased during episodes of invasive candidosis in immunosuppressed patients with a sensitivity of 65% [Greenfield R. A., Bussey, M. J, Stephens J. L, Jones J. M. Serial enzyme-linked immunosorbent assays for antibody to *Candida* antigens during induction chemotherapy for acute leukemia. J Infect Dis, 1983. 148(2): p. 275-83]. In a more recent study in immunocompromised patients anti-mannan antibodies increased within two weeks after the probable onset of invasive candidosis in contrast to patients that were only colonized with *C. albicans* [van Deventer A. J, Goessens W. H, van Zeijl J. H, Mouton J. W, Michel M. F, Verbrugh H. A. Kinetics of anti-mannan antibodies useful in confirming invasive candidiasis in immunocompromised patients. Microbiol Immunol, 1996. 40(2): p. 125-31]. A sensitivity of 64% was established in this study using a hemagglutination assay, which shows the highest efficiency with IgM antibodies. Since our results show no discriminatory effect of IgM antibodies, improved discrimination would be expected by using IgG antibody specific methods. Au-Young et al. showed that patients with systemic candidosis had elevated anti-mannan antibodies as tested by ELISA compared with patients with bacterial or other fungal infections [Au-Young J. K, Troy F. A, Goldstein E. Serologic analysis of antigen-specific reactivity in patients with systemic candidiasis. Diagn Microbiol Infect Dis, 1985. 3(5): p. 419-32]. The interpretation of the results was difficult, however, since two out of three patients with candiduria and one out of five controls had anti-mannan antibody levels comparable to those of the patients with systemic candidosis. In that study a slightly modified version of that of Peat et al. was used for the preparation of mannan and the antibodies were not analyzed with respect to their isotypes. Meckstroth et al. concluded that the ELISA titer of IgG antibody to mannan (prepared according to Peat et. al.) varied widely in leukemic patients irrespective of state of immuno-suppression or infection and was thus of no diagnostic value [Meckstroth K. L, Reiss E, Keller J. W, Kaufman L. Detection of antibodies and antigenemia in leukemic patients with candidiasis by enzyme-linked immunosorbent assay. J Infect Dis, 1981. 144(1): p. 24-32]. In view of our results and the reports using the mannan for antibody IgG analyses by ELISA, the specificity seems to improve with less modified mannan antigens such as our PPM which might be further enhanced with subclass IgG antibody analysis.

In contrast to PPM and Man, glucan with $\beta(1\text{-}3)(1\text{-}6)$D linkages was less effective in inhibiting the anti-CW antibody, suggesting that anti-glucan antibodies were not a major component in the rabbit immune serum. In addition, the anti-Glu antibodies were highly specific for $\beta(1\text{-}3)(1\text{-}6)$ linkages, since no inhibitory activity was observed by $\beta(1\text{-}4)(1\text{-}6)$ or $\beta(1\text{-}3)$ glucan. The anti-Glu levels in humans with candidemia were as low as for $CW_{IO4}$. Since $\beta(1\text{-}3)(1\text{-}6)$ glucan alone induces high antibody levels in immunized rabbits (authors unpublished results) our results are in agreement with the suggestion that glucan is located deeper in the cell wall of *C. albicans* and thereby less immunogenic [Sanjuan R, Zueco J, Zueco J, Perez J, Penarroja C, Sentandreu R. A comparative study of the incorporation of a 1,6-beta-glucan and an O-glycosylated protein epitope into the cell wall of *Candida albicans*. Microbiology, 1996. 142(Pt 8): p. 2255-62]. A stronger immunogenicity would probably require breakdown of the cell wall fragments and presentation by macrophages.

In summary, IgG antibodies to PPM and the native CW were found to be potential markers for detection of invasive *Candida* infection.

Experimental

Part II

Material and Methods

Study Group

Candidiasis. Serum samples were collected on two to three occasions after documentation of systemic candidiasis by culturing from 14 patients (mean age 62±12 years) (Table 2). The following criteria were applied when laboratory and clinical files were examined: (i) positive culture of specimens from normally sterile sites (blood, bile, drain, pericardial fluid); (ii) the presence of risk factors (cancer and chemotherapy, abdominal surgery or use of broad-spectrum antibiotics); (iii) the presence of infectious syndrome (fever) that did not respond to antibacterial therapy.

Controls. Two control groups were included in this study. One group (group I) comprised nine lactating mothers with superficial *C. albicans* infection of the nipples (mean age 31±5) and ten healthy blood donors (8 men and 2 women, mean age 53±7.5) (group II).

IgG Subclass Antibody Analysis.

Microplates (Nunc immunoplate, Denmark) were coated with 100 µl of a suspension of CW, PPM, Man or Glu, diluted in 50 mM $Na_2CO_3$ buffer, pH 9.3. The CW antigen was sonicated prior to coating in order to disaggregate the cell wall fragments which made the solution clearer. Optimal coating concentrations of CW, PPM, Man and Glu were determined by using the pool of rabbit antiserum diluted to 1/1000. Optimal concentrations were reached at 50, 5, 5 and 20 µg/ml of CW, PPM, Man and Glu, respectively. The plates were incubated at room temperature for 2 h, and thereafter kept at 4° C. overnight. After rinsing the plates once with PBS, 100 µl of blocking buffer (1% w/v BSA, 0.05% TWEEN™ 20 in PBS) were added to each well and incubated for 1 h at room temperature. The plates were rinsed once with 0.05% TWEEN™ 20 in PBS (PBS-T). Rabbit or human serum diluted in tenfold serial steps (1/100-1/10000) in PBS-T, was added to the wells (100 µl) in duplicates and incubated for 2 h at room temperature. After rinsing the plates three times with PBS-T, 100 µl of alkaline phosphatase-conjugated goat anti-rabbit or goat anti-human IgM or IgG were added to the wells. The conjugated anti-rabbit antibodies (Southern Biotechnology Associates, USA) were used at dilutions of 1/1000. The conjugated anti-human IgG and IgM (Jackson ImmunoResearch Laboratories, USA) were used in concentrations of 0.6 µg/ml. After incubation at room temperature for 2 h followed by rinsing, 100 µl of paranitrophenylphosphate (1 mg/ml, Sigma) diluted in diethanolamine buffer (pH 9.8) were added to each well. The absorbance was read at 405 nm after a suitable color intensity had developed.

The antibody titer of a serum was defined as the log of dilution that gave an absorbance value of 0.15 above the background value. Two serum samples were included in each assay as standards, one with a high antibody titer (pooled sera from patients) and another one with a low antibody titer (pooled sera from healthy individuals). If these standards deviated more than 10% from their values, the results were adjusted accordingly.

Glucan determination. The $\beta(1\text{-}3)$-glucan concentration in serum was determined by a commercial kit, GLUSPECY™ (Seikagaku, Japan). All glasswares were heated to 180° C. for 4 h in order to remove any contaminants. Serum samples were diluted 1/10 in pyrogen free water and heat inactivated at 75° C. for 10 min in order to inactivate inhibitory factors possibly present in the serum. Serum and standard samples were added to the microplate wells (50 µl) before pippeting 50 µl of lysate reagent into the wells. The plate was incubated at 37° C. for 30 min, then 50 µl of each of the azo-coupling reagents were added to the wells. The azo-coupling increased the sensitivity of the assay. The absorbance was read at 560 nm. The standard curve was plotted and $\beta(1\text{-}3)$-glucan concentration determined for each sample. The detection limit of the assay was 1 pg/ml and accordingly the detection limit was 10 pg/ml of the serum samples.

Mannan determination. For determination of mannan in serum a commercially available latex agglutination test *Candida*-PASTOREX™ (Sanofi Diagnostics Pasteur) was used. The assay was run according to the manufacture's instruction. To 300 µl of patient serum were added 100 µl of EDTA treatment solution and the mixture boiled for 3 min and centrifuged at 10 000×g for 10 min. Ten µl of *Candida* latex solution was added to 40 µl of supernatant. The solution was placed on a mixer for 10 min and thereafter examined for agglutination.

Statistical analysis. Data were analyzed by the method of Kruskal-Wallis to avoid random significance when comparing several groups. Correlations were analyzed by spearman's rank correlation test.

Results

Circulating Antigens

Figure 6:
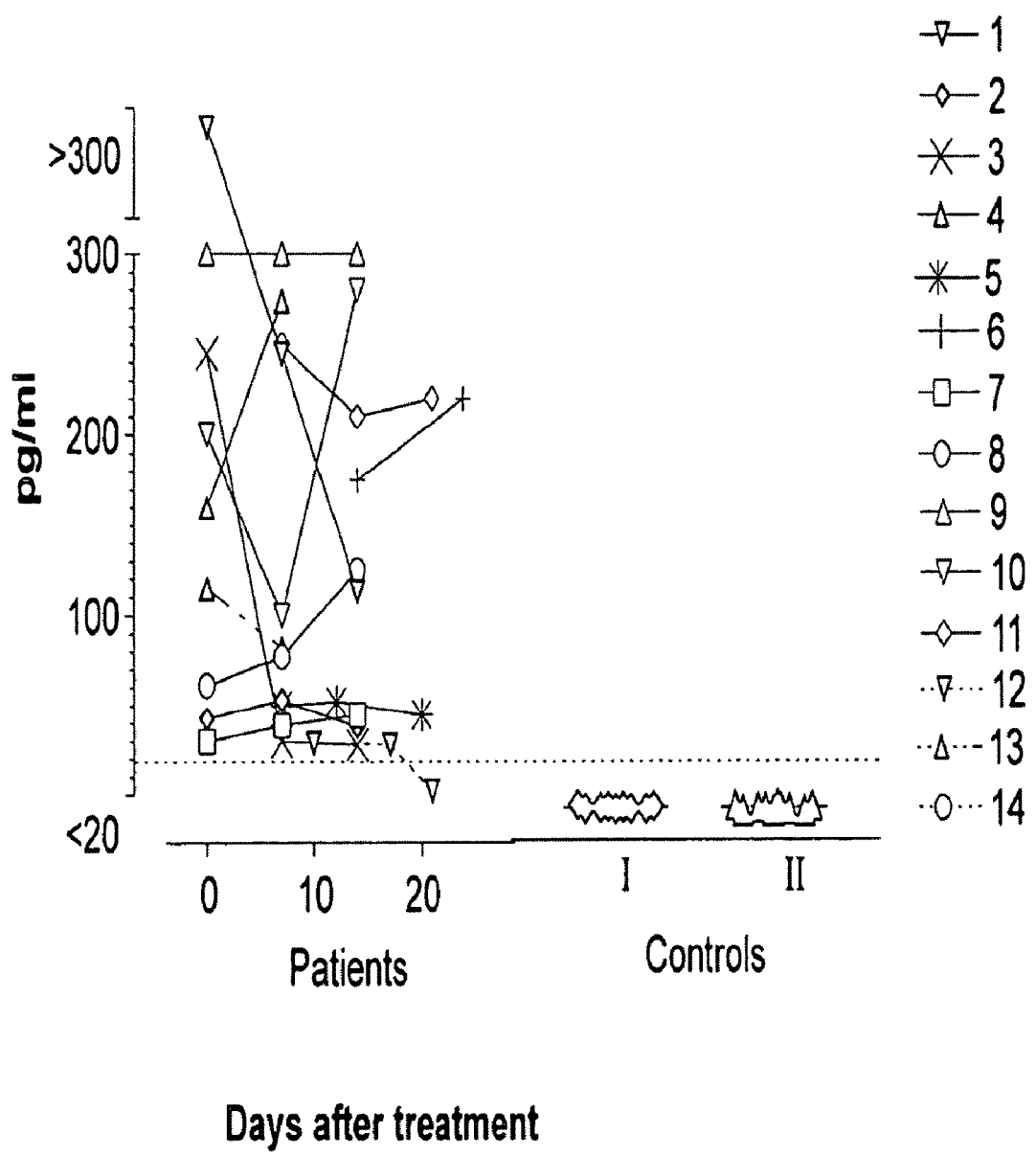
FIG. 6 illustrates glucan concentration in serum from patients with systemic candidiasis, superficial *Candida* infection (control group I), and healthy blood donors (group II) (a). Kinetics of the glucan concentration for each patient with respect to the time at which *Candida* was isolated (day 0) (b). The detection limit was 10 pg/ml as determined by GLUSPECY™.

Analysis of patients with candidiasis showed that 37 out of all 38 samples were positive (>20 pg/ml) for $\beta(1\rightarrow3)$-glucan (FIG. 6). The $\beta(1\text{-}3)$-glucan negative sample was however collected from the patient (patients 12) at least three weeks after the first cultivation of *C. tropicalis* from the patients (FIG. 6). Only one (patient 7) out of five patients (7, 8, 9, 10, 11) who succumbed to the *Candida* infection showed glucan concentrations below 100 pg/ml in all samples. The other four patients had levels of at least 120 pg/ml (FIG. 6). The other patients who survived had glucan levels lower than 100 pg/ml in their last serum sample except four of them (patient 1, 4, 5, 14). However, for one of these patients the glucan levels dropped in from over 300 to 110 pg/ml, probably indicating a successful recovery. The patient with the lowest glucan levels (no, 12, Table 1) were infected with *C. tropicalis*.

The concentrations of, β(13)-glucan in serum samples from patients with superficial fungal infection and from the healthy blood donors were all below 20 pg/ml (FIG. 6). Thus the concentration of β(1→3)-glucan in serum samples from patients with invasive candidiasis was significantly elevated compared to those in controls.

Patient and controls were also analysed for mannan by PASTOREX™ *Candida* assay. All of the patients and controls were negative.

IgG Subclass Antibodies Against *C. albicans* Cell Wall Antigens.

Figure 7A:
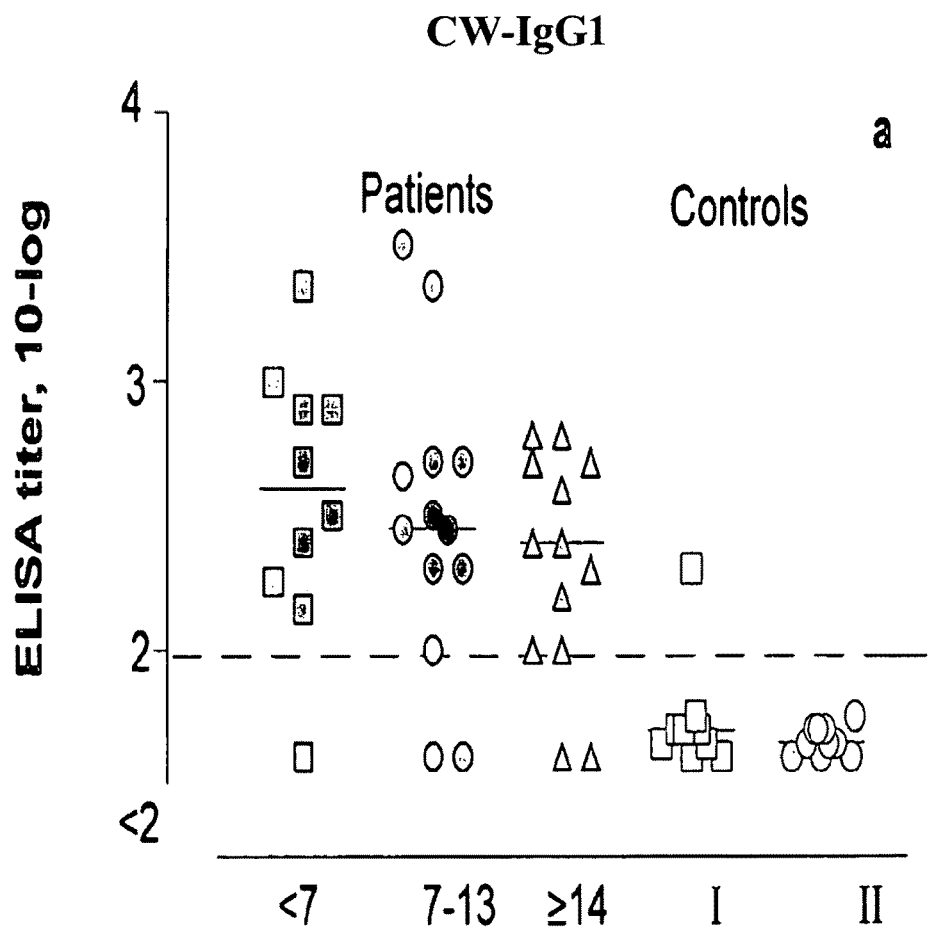
FIGS. 7*a* to 7*f* illustrate serum IgG1, IgG2, and IgG3 antibodies to *C. albicans* cell wall antigens in patients with systemic candidiasis and controls (group I and II). The antibody activity was analysed by ELISA (<2 log, no antibody activity in serum diluted 1:100).
Figure 8A:
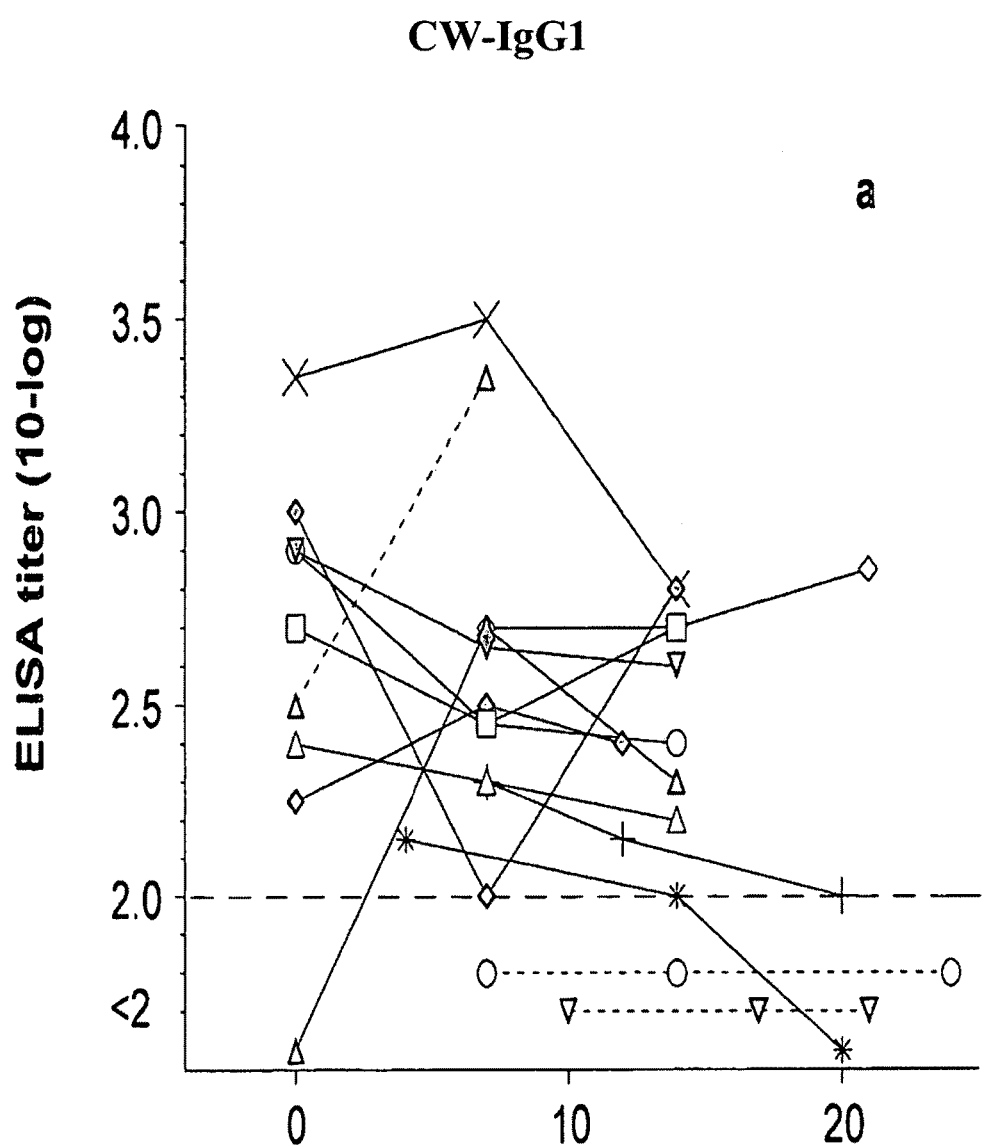
FIGS. 8*a* to 8*f* illustrate IgG1, IgG2, and IgG3 antibodies to *C. albicans* cell wall antigens in patients with systemic candidiasis at different time points after isolation of *Candida* from the patient. The antibody activity was analyzed by ELISA. Dashed lines indicate patients with non-albicans infections, open symbols indicate patients who did not survive the infection.

CW. The IgG subclass antibody analysis using *C. albicans* CW as antigen showed that IgG1, IgG2, and IgG3 antibodies were significantly elevated in patients compared to the control groups (FIGS. 7a, b, and c). All samples from two out of four patients (no. 12 and 14, Table 2) infected with *C. tropicalis* and *C. glabrata* were negative for IgG1 antibody to *C. albicans* CW (FIG. 8a). The highest antibody titers were found within the first week (<7) of culture-proven candidiasis. The titer of *C. albicans* infected patients were significantly higher than those of non-albicans infected ones for IgG1 antibodies to CW first after 14 days or more (p=0.049, not shown). Only one of the superficially *Candida* infected women in group I was positive for IgG1 antibodies to CW (FIG. 7a).

Figure 7B:
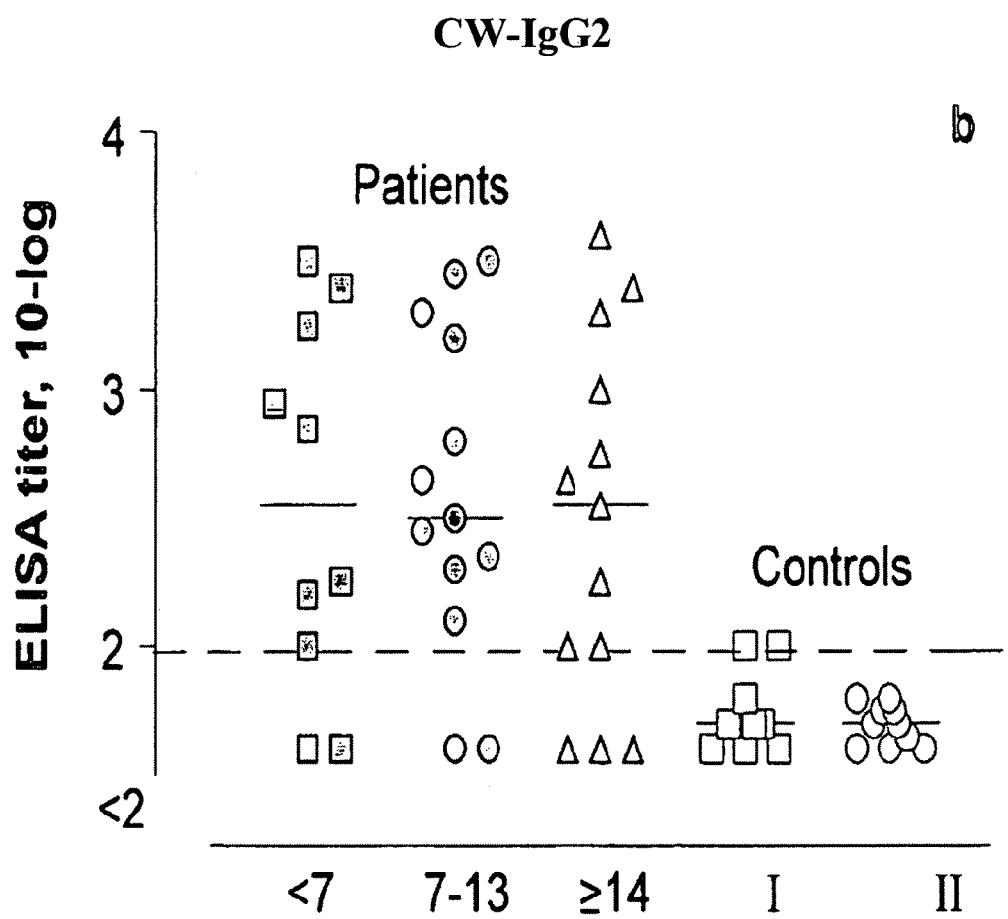
Figure 8B:
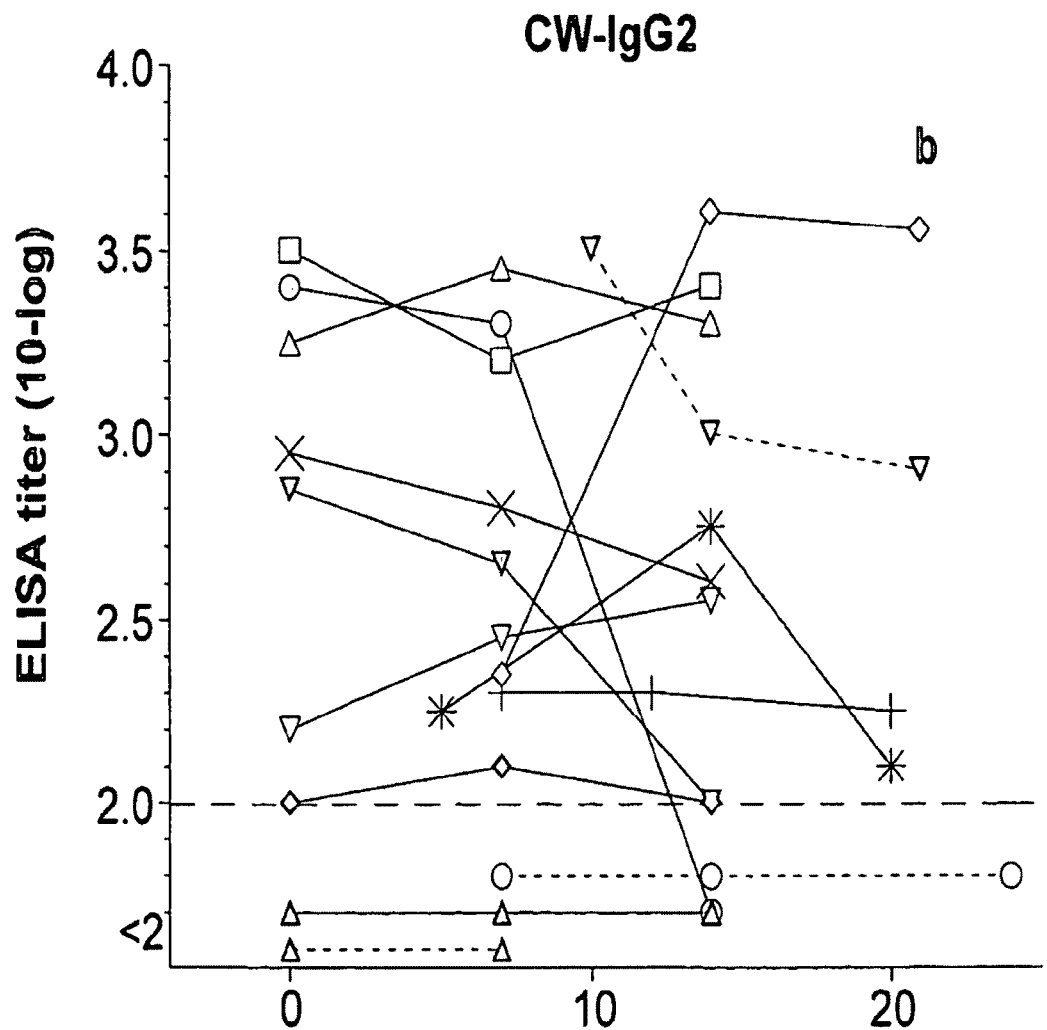

Three patients were negative for IgG2 antibodies to CW (FIG. 8b). Two out of these patients were infected with *C. glabrata* (FIG. 8b, Table 1). Two out of nine in control group I were shown positive values close to the border line for this antibody (FIG. 7b).

Figure 7C:
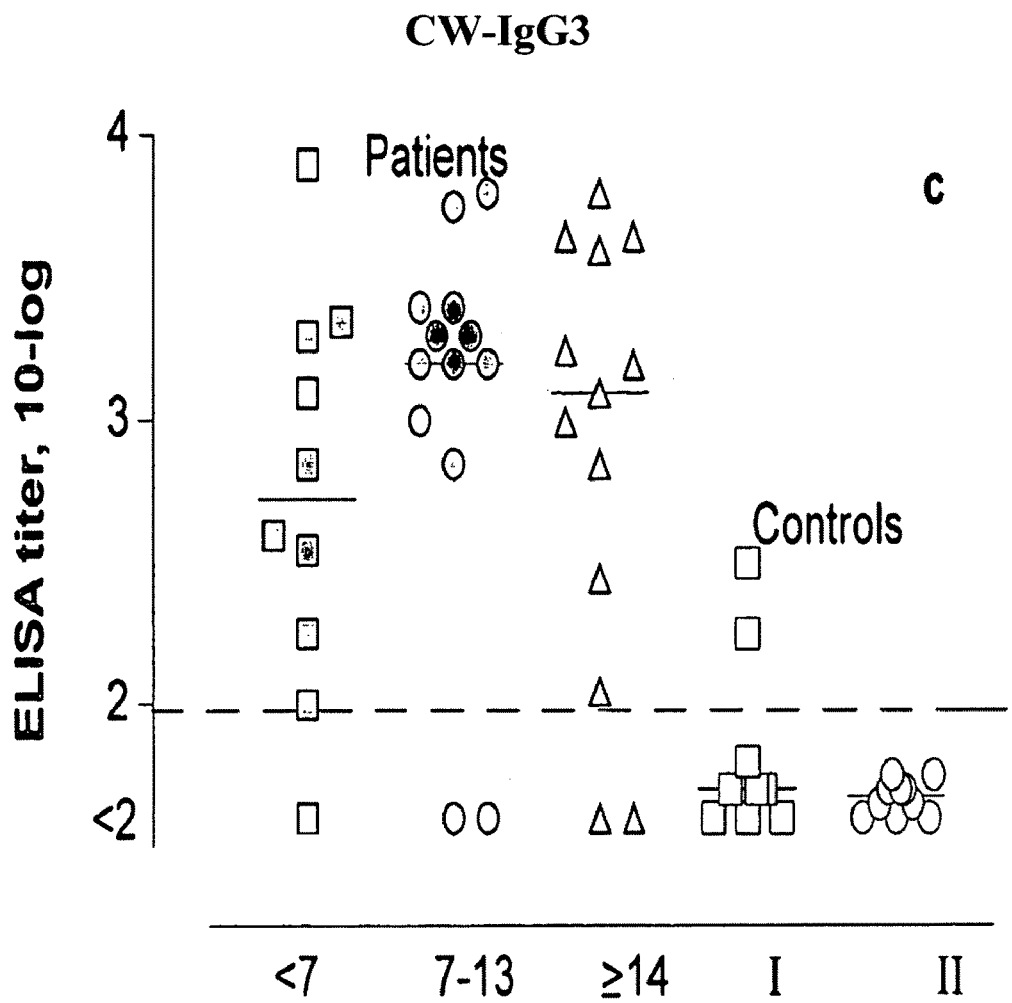
Figure 7D:
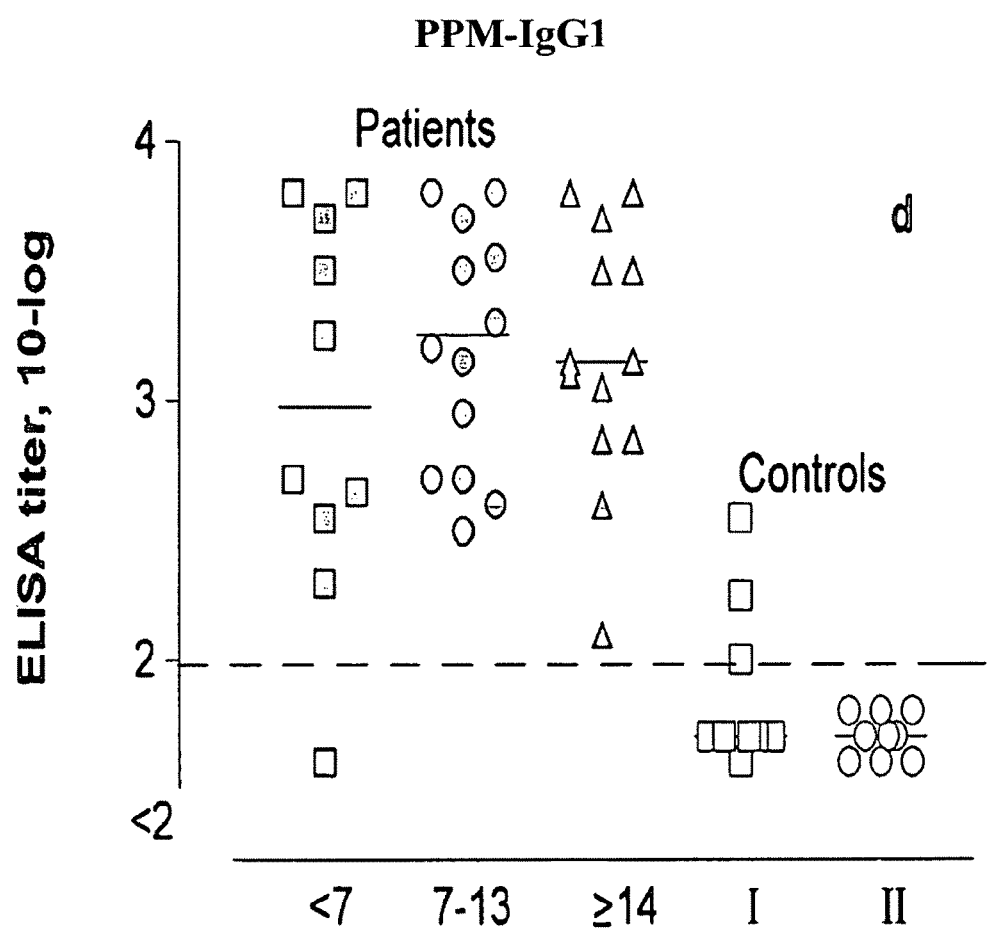
Figure 7E:
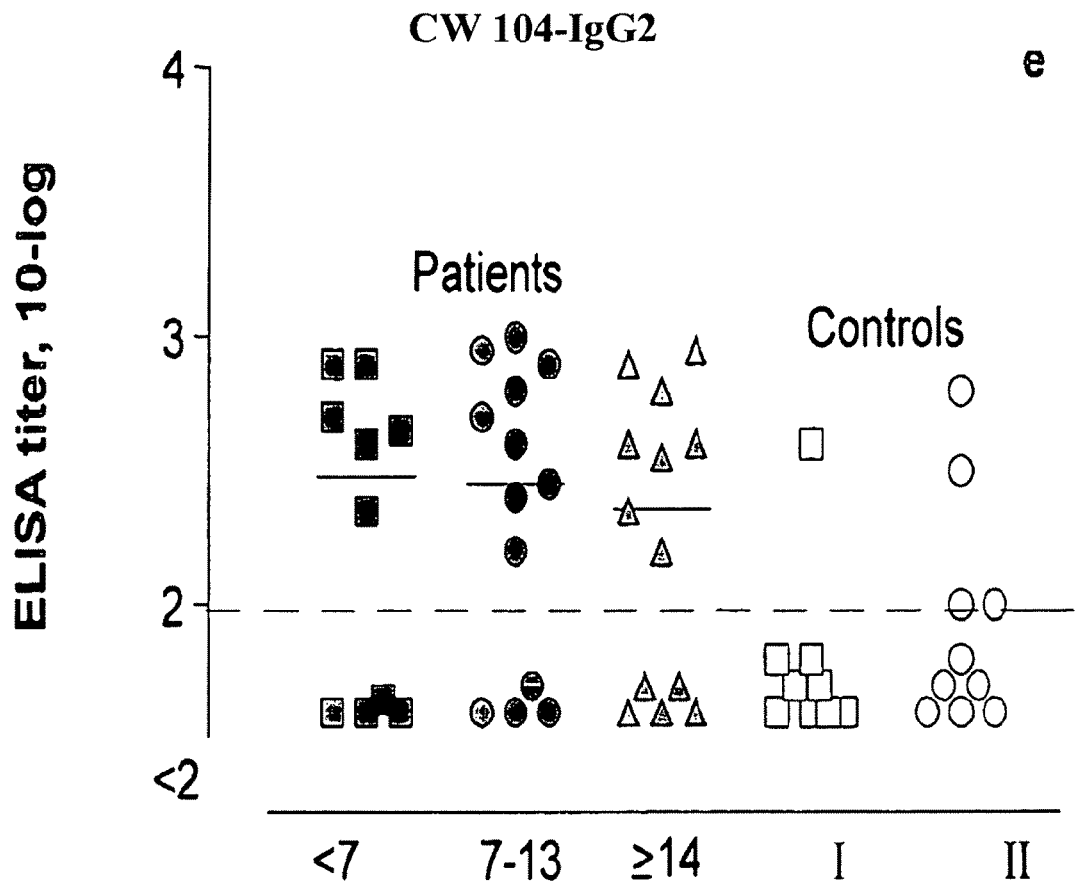
Figure 8C:
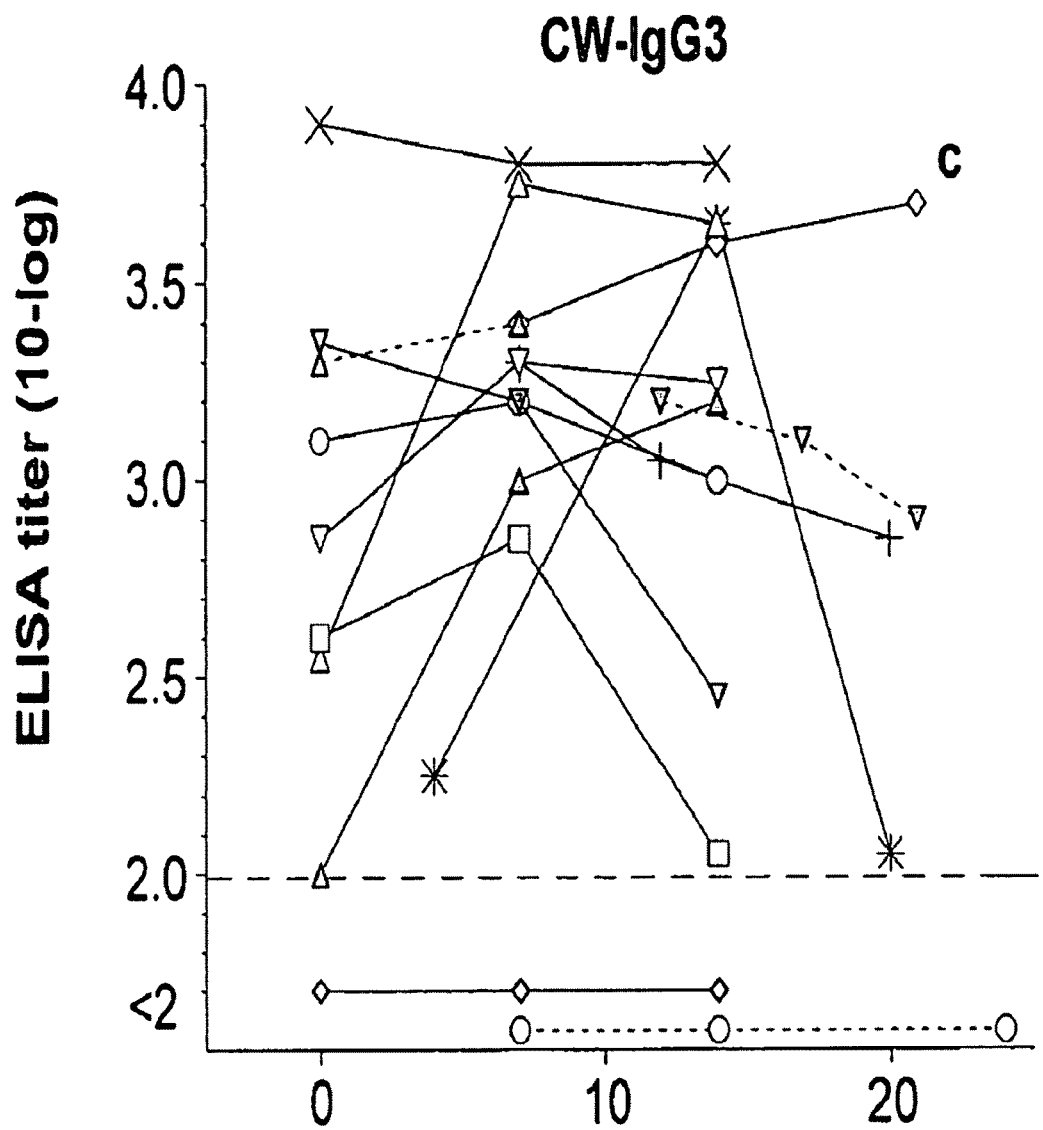
Figure 8D:
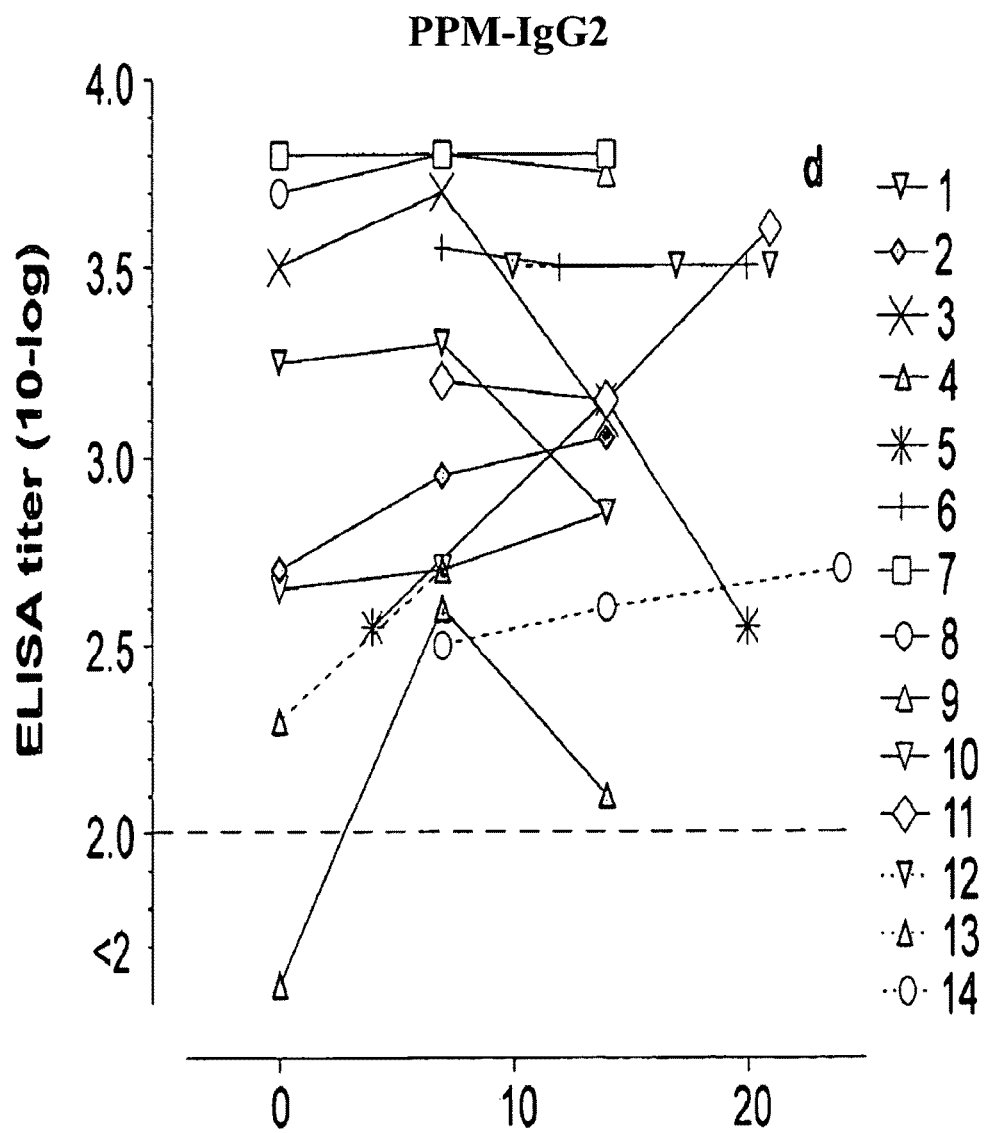
Figure 8E:
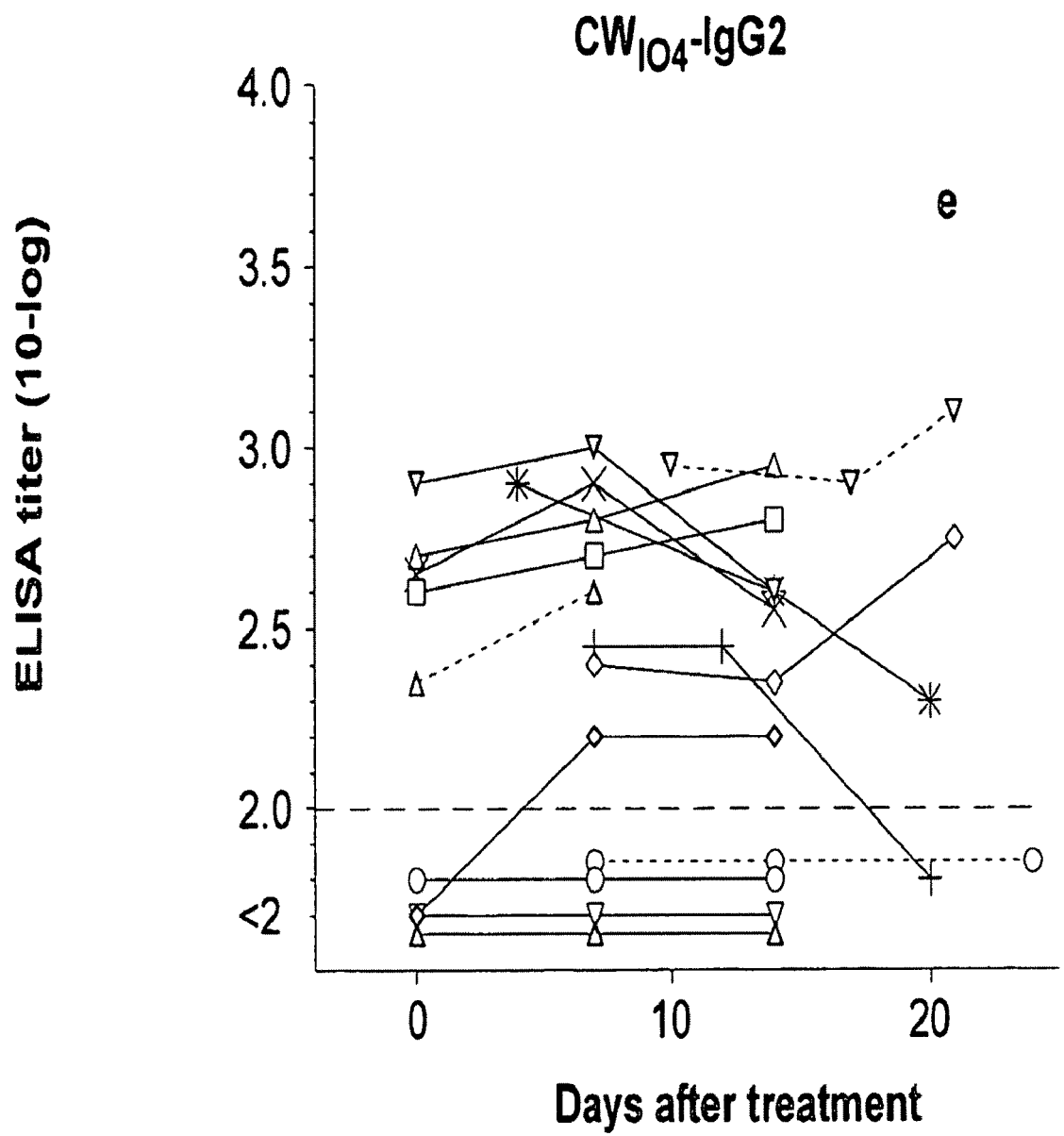

Regarding IgG3 antibodies to CW, one of the two patients who were negative was infected with *C. glabrata* (FIG. 8c). The highest IgG3 antibody titers were found between 7-13 days after positive blood cultures (FIG. 7c). All the healthy blood donors were negative for IgG3 antibodies, while two women with superficial *Candida* infection in group I were positive. No differences (P>0.05) were found between the patients and the controls regarding IgG4 and IgM antibodies to CW. The ELISA titer were usually very similar in patients as well as controls (data not shown).

$CW_{IO4}$, glucan, and PPM. Concerning IgG1, IgG3 and IgG4 antibodies to $CW_{IO4}$, glucan, and PPM no discriminatory differences were found between the patients and the controls (data not shown). Differences between patients and controls were found, however for IgG2 antibodies to these antigens (FIG. 7 d, e, f and Table 3).

For the two last sampling points in patients (≧7-13, and ≧14) the levels of IgG2 antibodies to $CW_{IO4}$ were significantly higher when compared with control group I (FIG. 7 e). Four patients were negative, and one of these did not survive (FIG. 8 e). In addition, all four presented increased glucan values with time (P=0.0037, Fischer's exact test).

IgG2 antibodies to PPM were significantly increased in patients compared to the controls (FIG. 7 d, table 3). All of the patients were positive for IgG2 antibody to PPM (FIG. 8 d). Only one serum sample was negative within the first week. This very early serum sample was negative in other antibody tests. However, also three controls in group I were positive for IgG2 antibodies to PPM, while all of the healthy blood donors were negative (FIG. 7 d). Looking at the ratios of IgG1 anti-CW/IgG2 anti-PPM they were significantly lower in non-surviving patients than in the other patients, especially within the first week (<7) after the cultivation of *Candida* from blood (P=0.019, not shown).

Figure 7F:
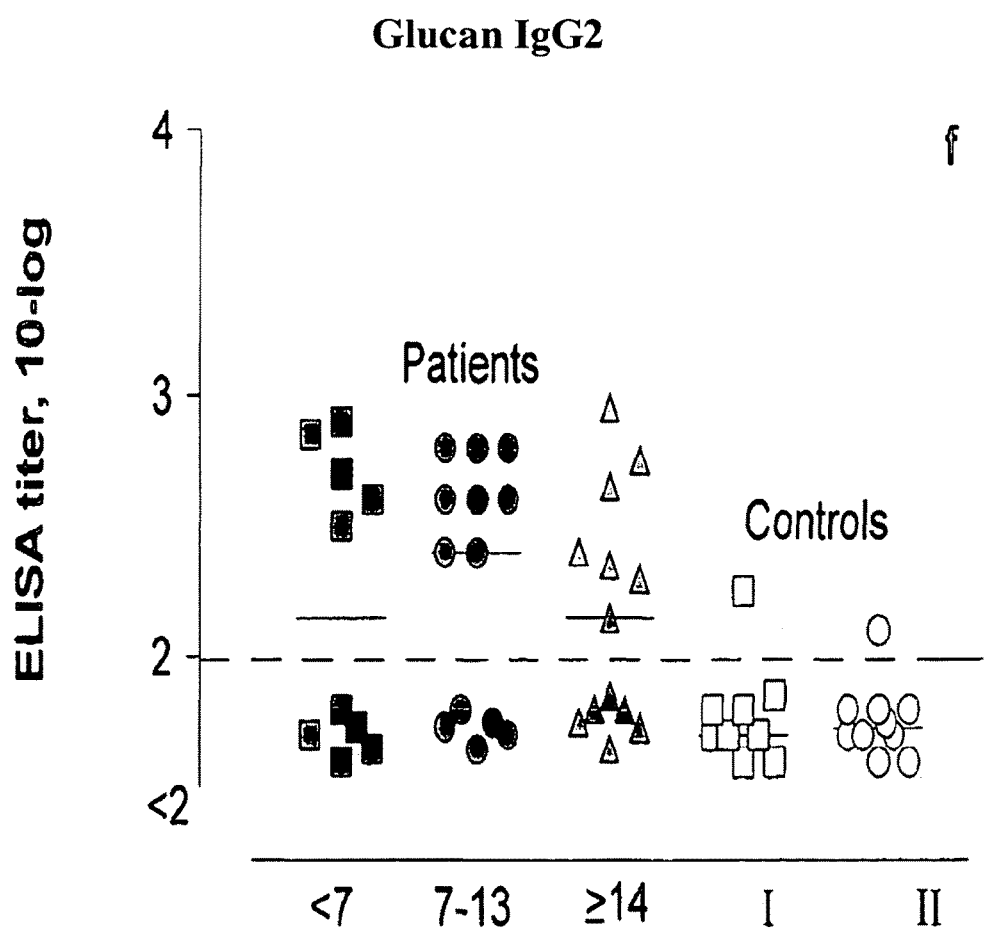
Figure 8F:
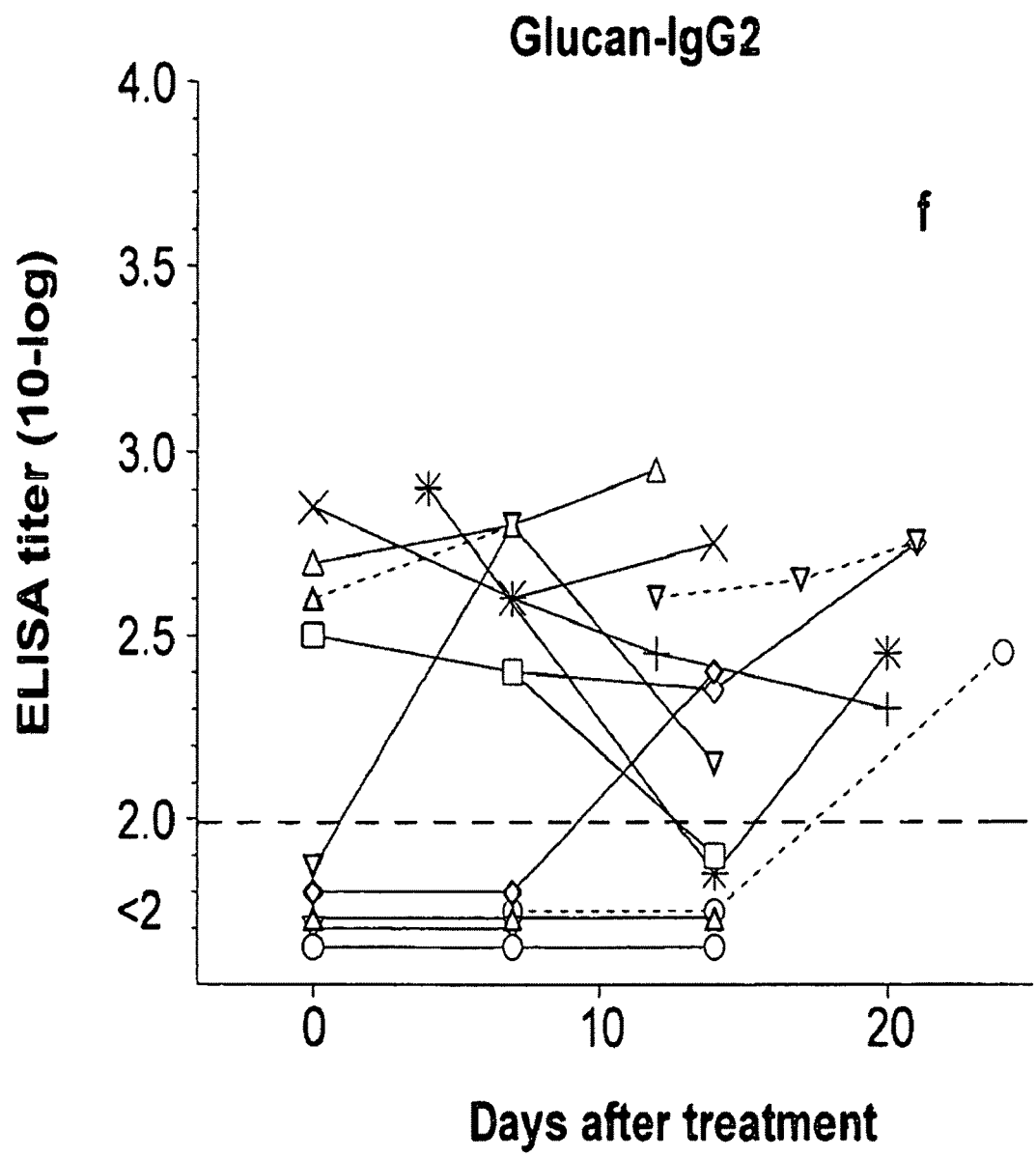

IgG2 antibodies to glucan were also significantly higher compared to the controls except when comparing the serum samples of <7 days (FIG. 7f). Three patients, all infected with *C. albicans*, were negative at all time points and were the same as found negative for IgG anti-$CW_{IO4}$ antibodies (FIG. 8f). One of the controls in group I and another one in group II were positive (FIG. 7f).

A strong correlation was found between IgG2 antibodies to CW and PPM (Table 3), and between IgG2 antibodies to $CW_{IO4}$ and glucan (P<0.0001, not shown) reflecting the predominating PPM antigen in CW and the glucan content of $CW_{IO4}$, respectively. No correlation was observed between IgG1 anti-CW and the IgG2 anti-$CW_{IO4}$, -PPM, and -glucan antibodies indicating that the IgG1 antibodies are directed against other antigenic epitopes in the CW (Table 3).

No significant correlation was found between glucan concentration in serum and any IgG subclass antibody. However glucan correlated with IgM antibodies to CW (P<0.0001).

The sensitivity, specificity, positive and negative predictive values of the antibody detection tests were calculated (Table 5). The sensitivity of IgG2 antibody detection test increased from 85% for CW to 98% when PPM was used. The sensitivity of IgG1 and IgG3 antibodies to CW were almost the same (80% and 85% respectively). The lowest specificity was found for IgM antibodies to CW, which makes these antibodies of no diagnostic value.

It is important to be able to distinguish patients with systemic candidiasis from other infections as early as possible after the onset of clinical symptoms. For this reason the discriminatory power of the combination of the most sensitive method (IgG2 anti-PPM) with the most specific one (IgG1 anti-CW antibody) was analyzed (Table 4). A positive serum sample was defined as either a titer of log 3 for any of the two antibodies or a log sum of at least 5. Although the sensitivity was 70% within the first week (<7) of culture-proven candidiasis, the combination of these antibodies increased the specificity and positive predictive value to 100%. Although the glucan concentration on its own identified all candidiasis cases, this parameter together with the combined IgG2 anti-PPM and IgG1 anti-CW antibodies strongly support a deep *candida* infection.

TABLE 1

Chemical analysis of *C. albicans* cell wall preparations, PPM, Man, and glucans.

| Antigens | Amount, % of dry weight | | |
|---|---|---|---|
| | Hexose | Protein | Phosphate |
| CW | 93 | 16 | 0.27 |
| $CW_{IO4}$ | 83 | (60=) | 0.84 |
| $CW_P$ | 90 | 8 | 0.11 |
| PPM | 95 | 10 | 0.83 |
| Man | 99 | 2.4 | 0.002 |
| Glu | 100 | 6 | 0.03 |
| Glu-B | 100 | 0 | 0.10 |
| Glu-C | 100 | 0 | ND* |

*Not determined.
=The $CW_{IO4}$ was not soluble in the protein assay and thus the absorbance showed too high value due to turbidity.

TABLE 2

Underlying diseases and culture data of patients indicated in the systemic candidiasis.

| Patient no | Sex* | Age (yr) | Hospital ward | Underlying Condition | No of serum specimens | Candida Cultured from | Candida Species | Outcome |
|---|---|---|---|---|---|---|---|---|
| 1 | F | 71 | ICU | Rectal neoplasms | 3 | Blood | C. albicans | survived |
| 2 | F | 67 | Surgery | Pancreaticoduodenectomy | 3 | Blood | C. albicans | survived |
| 3 | F | 40 | Neurology | Aneurysm | 3 | Blood | | survived |
| 4 | M | 74 | ICU | Aortic aneurysm | 3 | Blood | C. albicans | survived |
| 5 | M | 61 | ICU | Diabetes mellitus hemorrhagic pancreatitis | 3 | Blood | C. albicans | survived |
| 6 | F | 56 | E*** | E | 3 | Blood | C. albicans | survived |
| 7 | F | 74 | ICU | Diabetes mellitus | 3 | Blood | C. albicans | >** |
| 8 | F | 50 | Surgery | Non-Hodgkin's lymphoma | 3 | Blood | C. albicans | > |
| 9 | F | 47 | ICU | Neoplasm, Intestinal obstruction | 3 | Blood | C. albicans | > |
| 10 | M | 66 | Transplantation Unit | Diabetic angiopathies and nephropathies | 3 | Abdominal | C. albicans | > |
| 11 | M | 66 | Thorax | Atrial fibrillation | 3 | Blood | C. albicans | > |
| 12 | F | 82 | Transplantation Unit | Gallbladder neoplasms | 3 | Blood | C. tropicalis | survived |
| 13 | M | 64 | Surgery | Diabetic coma | 2 | Blood/Drain | C. glabrata | survived |
| 14 | F | 46 | Transplantation Unit | Hepatitis B and hepatitis C | 3 | Bile | C. glabrata | survived |

*M, male; F, female.
**>Dead
***Epatient was described with Candida septicaemia. (sepsis)

TABLE 3

The correlation between IgG2 antibodies in serum sample from patients with systemic candidiasis. The correlation was calculated by Spearman's rank correlation test.

| | IgG2 | | | |
|---|---|---|---|---|
| | CW | $CW_{IO4}$ | PPM | Glucan |
| CW- IgG1 | ns | ns | ns | ns |
| CW- IgG2 | — | 0.0010 | <0.0001 | ns |
| CW- IgG3 | 0.0372 | 0.0191 | 0.0484 | 0.0077 |
| CW- IgM | 0.0069 | ns | 0.0317 | ns |

TABLE 4

Sensitivity, specificity and predictive values for the detection of subclass antibodies in patients with systemic candidiasis.

| Parameters[a] % | CW IgG1 | CW IgG2 | CW IgG3 | CW IgM | PPM IgG2 | $CW_{IO4}$ IgG2 | Glucan IgG2 |
|---|---|---|---|---|---|---|---|
| Sensitivity | 80 | 85 | 85 | 90 | 98 | 66 | 61 |
| Specificity | 95 | 89 | 89 | 26 | 95 | 74 | 89 |
| Positive Predictive Value | 97 | 94 | 95 | 74 | 93 | 85 | 93 |
| Negative Predictive Value | 69 | 74 | 74 | 56 | 95 | 50 | 52 |

[a]Results are calculated per serum according to the analysis of 41 serum samples from 14 patients with systemic candidiasis, and 19 serum samples from controls.

TABLE 5

Sensitivity, specificity, and predictive values for combined detection of IgG1 anti-CW and IgG2 anti-PPM antibodies at different time points after culture-proven Candidiasis.

| | Combination of IgG1 anti-CW and IgG2 anti-PPM* | | |
|---|---|---|---|
| Parameters[a] | <7 days | 7-13 days | >14 days |
| Sensitivity | 70 | 92 | 85 |
| Specificity | 100 | 100 | 100 |
| Positive predictive value | 100 | 100 | 100 |
| Negative predictive value | 86 | 95 | 90 |

[a]Results are calculated per serum according to the analysis of serum samples from patients with systemic candidiasis, and 19 serum samples from controls.
*In order to be positive the titer of any of the two antibodies had to be either equal to or exceed log 3, or the combined values equal to or more than log 5.

Discussion

The diagnosis of invasive candidiasis is extremely difficult, both clinically and microbiologically (Jones, J. M. 1990. Laboratory diagnosis of invasive candidiasis. Clin Microbiol Rev 3:32-45). To solve this problem, serological diagnostic methods based on detection of marker substances as well as antibodies to Candida have been used (de Repentigny, L., R. J. Kuykendall, F. W. Chandler, J. R. Broderson, and E. Reiss. 1984. Comparison of serum mannan, arabinitol, and mannose in experimental disseminated candidiasis. J Clin Microbiol 19:804-12; Gutierrez, J., C. Maroto, G. Piedrola, E. Martin, and J. A. Perez. 1993. Circulating Candida antigens and antibodies: useful markers of candidemia. J Clin Microbiol 31:2550-2; Obayashi, T., M. Yoshida, T. Mori, H. Goto, A.

Yasuoka, H. Iwasaki, H. Teshima, S. Kohno, A. Horiuchi, A. Ito, and et al. 1995. Plasma (1→3)-beta-D-glucan measurement in diagnosis of invasive deep mycosis and fungal febrile episodes. Lancet 345:17-20; Reiss, E., T. Obayashi, K. Orle, M. Yoshida, and R. M. Zancope-Oliveira. 2000. Non-culture based diagnostic tests for mycotic infections. Med Mycol 38:147-59). Some of these techniques are commercially available, but their clinical reliability of these products is still controversial. In the present study glucan determination and analysis of IgG1 anti-CW and IgG2 anti-PPM antibodies were found to be reliable and early markers of systemic candidiasis. All patients within the first two weeks of systemic candidiasis were positive for glucan. The glucan concentrations in all controls were below the cut-off value (<20 pg/ml). Likewise, patients with IgG1 anti-CW or IgG2 anti-PPM with a high titer ($\geq$log 3), or the combined titer of the antibodies (titer$\geq$log 5) showed 92% sensitivity and 100% specificity.

These results show the potential value of antibodies in the laboratory assessment of patients with systemic candidiasis, which is in agreement with others (Sendid, B., M. Tabouret, J. L. Poirot, D. Mathieu, J. Fruit, and D. Poulain. 1999. New enzyme immunoassays for sensitive detection of circulating Candida albicans mannan and antimannan antibodies: useful combined test for diagnosis of systemic candidiasis. J Clin Microbiol 37:1510-7; van Deventer, A. J., W. H. Goessens, J. H. van Zeijl, J. W. Mouton, M. F. Michel, and H. A. Verbrugh. 1996. Kinetics of anti-mannan antibodies useful in confirming invasive candidiasis in immunocompromised patients. Microbiol Immunol 40:125-31). With our CW and PPM antigens all patients with systemic candidiasis except one were positive in their antibody levels within the first week of their infection. The highest IgG2 anti-PPM antibodies were found whithin 7-13 days after cultivation of Candida, which is in agreement with van Deventer et al. who observed that anti-mannan antibody titer in immunocompromised patients with invasive candidiasis increased within two weeks after the possible onset of invasive candidiasis. (van Deventer, A. J., W. H. Goessens, J. H. van Zeijl, J. W. Mouton, M. F. Michel, and H. A. Verbrugh. 1996. Kinetics of anti-mannan antibodies useful in confirming invasive candidiasis in immunocompromised patients. Microbiol Immunol 40:125-31). Sendid et al. showed that combined test for detection of circulating mannan and anti-mannan antibodies is useful for detection of patients with systemic candidiasis, with the sensitivity and specificity of 80 and 93% which were calculated per patient, when at least one serum was positive by one of the tests. Sendid et al. demonstrated that seum samples with high concentration of circulating mannan had a low level of antimannan antibodies and vice versa (Sendid, B., M. Tabouret, J. L. Poirot, D. Mathieu, J. Fruit, and D. Poulain. 1999. New enzyme immunoassays for sensitive detection of circulating Candida albicans mannan and antimannan antibodies: useful combined test for diagnosis of systemic candidiasis. J Clin Microbiol 37:1510-7). The inventors did not find any association of circulating glucan and IgG2 anti-glucan, PPM and CW in serum. However, a very significant correlation was found between circulating glucan and IgM anti-CW antibodies.

Patients, who did not survive the fungal infection had significantly lower ratios of IgG1 anti-CW to IgG2 anti-PPM antibodies during the first week after isolation of Candida. That high concentration of IgG2 antibodies may interfere with binding of IgG1 or IgG3 and thereby diminishing or preventing the bacteria from being properly phagocytosed has been suggested for patients with high IgG2 antibodies to P. aeruginosa in cystic fibrosis (Pressler, T., B. Mansa, T. Jensen, S. S. Pedersen, N. Hoiby, and C. Koch. 1988. Increased IgG2 and IgG3 concentration is associated with advanced Pseudomonas aeruginosa infection and poor pulmonary function in cystic fibrosis. Acta Paediatr Scand 77:576-82).

No consistent difference was found in the different antibody responses to the C. albicans cell wall antigens between patients infected with C. albicans and those infected with other Candida species. This is not surprising, since mannans of different Candida species have similar structures and share common epitopes, which cross-react with antibodies to C. albicans (Suzuki, S. 1997. Immunochemical study on mannans of genus Candida. I. Structural investigation of antigenic factors 1, 4, 5, 6, 8, 9, 11, 13, 13b and 34. Curr Top Med Mycol 8:57-70). The inventors have observed that serum from rabbits immunized with C. albicans cross-reacts with PPM extracted from C. glabrata and C. parapsilosis. However out of the seven altogether negative anti-CW tests encompassing IgG1, IgG2 and IgG3 antibodies five represented all the patients infected with non-albicans Candida species. This might be a result of species differences with respect to CW antigens. Furthermore, failure of anti-CW IgG1, IgG2 or IgG3 antibody response may be an indication to use anti-fungal treatment covering non-albicans species, whereas when the titers of all these substances are significant anti-albicans treatment should suffice.

The time required for diagnosis of systemic candidiasis is an important factor in decreasing the mortality among these patients. Thus, a high positive predictive value of the glucan and antibody analyses at the onset of systemic candidiasis is of help when initiating an early treatment by antifungal. The treatment of patients with invasive fungal infections by antifungal agents, however, is limited and does not differ much with the fungal species. It may therefore be more practical to analyse a blood sample for fungal antigens such as β(1→3)-glucan and antibodies first and if these parameters are positive start antifungal therapy immediately, while searching for fungal species. By this strategy the mortality among patients with invasive fungal infections may be decreased.

In conclusion, our results suggest that the combination of IgG2 anti-PPM, IgG1 and IgG3 anti CW constitute a reliable laboratory tests to diagnose patients with systemic candidiasis in an early stage.

The invention claimed is:

1. A method of serodiagnosis of early stage invasive candidiasis in a patient comprising:
    performing a serological assay in a serum sample of the patient for the detection of IgG2 antibody to a phosphopeptidomannan fraction of the cell wall of Candida albicans, and IgG1 antibody to native a Candida albicans cell wall antigen, and beta (1-3) glucan using the serum sample of the patient, wherein:
    (a) the simultaneous detection of the serum IgG2 antibody to the phosphopeptidomannan fraction of the cell wall of Candida albicans, and the serum IgG1 antibody to the native Candida albicans cell wall antigen with a significantly increased antibody level for the IgG1 antibody to the native Candida albicans cell wall antigen and the IgG2 antibody to the phosphopeptidomannan fraction of the cell wall antigen of the Candida albicans, compared to titers of serum antibodies of healthy human controls to said antigens, and (b) the simultaneous detection of the beta (1-3) glucan in the serum sample indicate the serodiagnosis of the early stage invasive candidiasis in the patient.

* * * * *